US012648920B2

(12) United States Patent
Greene et al.

(10) Patent No.: US 12,648,920 B2
(45) Date of Patent: Jun. 9, 2026

(54) METHODS OF ADMINISTERING GLUTATHIONE PRECURSORS

(71) Applicant: Neuronasal, Inc., Wexford, PA (US)

(72) Inventors: Douglas A. Greene, Basking Ridge, NJ (US); Thomas I. Bradshaw, Wynnewood, PA (US)

(73) Assignee: Neuronasal, Inc., Wexford, PA (US)

( * ) Notice: Subject to any disclaimer, the term of this patent is extended or adjusted under 35 U.S.C. 154(b) by 0 days.

(21) Appl. No.: 18/172,242

(22) Filed: Feb. 21, 2023

(65) Prior Publication Data

US 2024/0024267 A1 Jan. 25, 2024

Related U.S. Application Data

(63) Continuation of application No. PCT/US2021/046992, filed on Aug. 20, 2021.

(60) Provisional application No. 63/116,404, filed on Nov. 20, 2020, provisional application No. 63/068,513, filed on Aug. 21, 2020.

(51) Int. Cl.

| | |
|---|---|
| ***A61K 31/198*** | (2006.01) |
| ***A61K 9/00*** | (2006.01) |
| ***A61K 47/10*** | (2017.01) |

(52) U.S. Cl.

CPC .......... *A61K 31/198* (2013.01); *A61K 9/0043* (2013.01); *A61K 47/10* (2013.01)

(58) Field of Classification Search

CPC .............................. A61K 31/198; A61K 47/10

See application file for complete search history.

(56) References Cited

U.S. PATENT DOCUMENTS

| | | | | |
|---|---|---|---|---|
| 2006/0257488 | A1 * | 11/2006 | Hubbard | A61K 9/0024 524/502 |
| 2010/0004210 | A1 * | 1/2010 | Roecken | A61P 37/08 435/6.16 |
| 2011/0076261 | A1 * | 3/2011 | Patel | A61K 31/56 514/159 |
| 2011/0319442 | A1 * | 12/2011 | Leoni | A61P 13/10 514/293 |
| 2013/0115181 | A1 * | 5/2013 | Otero Espinar | A61K 47/10 424/61 |
| 2015/0030681 | A1 * | 1/2015 | Merry | C12N 5/0663 435/177 |
| 2020/0214285 | A1 * | 7/2020 | Tsushima | C11D 3/48 |

OTHER PUBLICATIONS

Srivastava, R. et al. "Thermoreversible In-Situ Nasal Gel Formulations and Their Pharmaceutical Evaluation for the Treatment of Allergic Rhinitis Containing Extracts of Moringa Olifera and Embelia Ribes" (Int J App Pharm 9 (6) 2017, 16-20) (Year: 2017).*

* cited by examiner

*Primary Examiner* — Andrew S Rosenthal
(74) *Attorney, Agent, or Firm* — FBT Gibbons LLP

(57) ABSTRACT

The present disclosure describes methods of administering a pharmaceutical composition comprising a glutathione precursor and a thermoresponsive polymer via intranasal administration. In some embodiments, intranasal administration of the glutathione precursor can be used to treat a condition, for example, a central nervous system disorder.

7 Claims, No Drawings

METHODS OF ADMINISTERING GLUTATHIONE PRECURSORS

CROSS-REFERENCE

This application is a continuation of International Application No. PCT/US21/46992, filed Aug. 20, 2021, which claims the benefit of U.S. Provisional Application No. 63/068,513, filed Aug. 21, 2020, and U.S. Provisional Application No. 63/116,404, filed Nov. 20, 2020, which are incorporated herein by reference in their entirety.

BACKGROUND

NAC is a precursor of L-cysteine that results in glutathione elevation biosynthesis. NAC is a powerful antioxidant that acts directly as a scavenger of free radicals, for example, oxygen free radicals. NAC can be used as a treatment option for disorders resulting from the generation of free oxygen radicals. NAC has a range of pleotropic salutary effects on acute and chronic central nervous system (CNS) disorders. Formulations to effective administer NAC to the brain are necessary to improve the therapeutic use of NAC.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, disclosed herein is a pharmaceutical composition comprising: a) a glutathione precursor; b) a thermoresponsive polymer; and c) a viscosity modifying agent. In some embodiments, disclosed herein is a method of treating a condition, the method comprising administering a therapeutically-effective amount of a pharmaceutical composition to a subject, the pharmaceutical composition comprising: a) a glutathione precursor; and b) a thermoresponsive polymer, wherein the administering is intranasal.

In some embodiments, disclosed herein is a method of treating a condition, the method comprising administering a therapeutically-effective amount of a pharmaceutical composition to a subject in need thereof, the pharmaceutical composition comprising: a) a glutathione precursor; b) a thermoresponsive polymer; and c) a viscosity modifying agent.

In some embodiments, disclosed herein is a method of treating a condition, the method comprising administering a therapeutically-effective amount of a pharmaceutical composition to a subject in need thereof, the pharmaceutical composition comprising: a) a glutathione precursor; and b) a thermoresponsive polymer, wherein the condition is a central nervous system condition.

In some embodiments, disclosed herein is a method of treating a condition, the method comprising administering a therapeutically-effective amount of a pharmaceutical composition to a subject in need thereof, the pharmaceutical composition comprising: a) a glutathione precursor; and b) a thermoresponsive polymer, wherein the condition is a head condition.

In some embodiments, disclosed herein is a method of treating a condition, the method comprising administering a therapeutically-effective amount of a pharmaceutical composition to a human subject in need thereof, the pharmaceutical composition comprising: a) a glutathione precursor; and b) a thermoresponsive polymer.

DETAILED DESCRIPTION OF THE INVENTION

Pharmaceutical treatment of acute and chronic diseases of the central nervous system (CNS) is greatly hindered by the relatively impermeable blood brain barrier (BBB) and blood cerebrospinal fluid barrier (BCSFB), which exclude 95% of therapeutic molecules from entering the CNS from the bloodstream. An alternate delivery route to reach the CNS that circumvents the BBB and BCSFB leverages discrete anatomical and functional connections between the nasal cavity and structures within the brain, and is termed "nose-to-brain" (N2B) drug delivery. The functional connections between the nasal cavity and structures within the brain are functionally and structurally subdivided into those mediated by transcellular, paracellular, and intracellular transport, beginning in the respiratory or olfactory epithelium of the nose and proceeding along the trigeminal or olfactory nerve pathways or associated lymphatics or the rostral migratory pathway. The different anatomical and functional pathways can deliver cargoes with distinctly different cadence and to different regions within the CNS.

Concussions, also known as mild traumatic brain injuries (mTBIs), are transient and clinically detectable alterations in brain function resulting from mechanical insult transmitted to the brain. The global incidence of mTBI is approximately 42 million persons per year, with 100 to 300 per 100,000 individuals seeking medical attention annually. The risk of mTBI, as well as repetitive mTBI and sub-concussive injuries, is increased for subpopulations such as military personnel, athletes and victims of domestic abuse. Civilian mTBI can result from blunt trauma sustained in accidents, assaults, or participation in athletic activities. The Centers for Disease Control (CDC) estimates that there 1.6 to 3.8 million sports- and recreation-related concussions each year in the US. The direct and indirect costs attributable to concussions have been estimated at over $17 billion annually in the U.S. alone.

For military personnel, blast injury is a frequent cause of concussion and more severe head injuries. Seventy-five percent of the head injuries due to explosive blasts are classified as mild. The incidence of military mTBI between 1997 and 2007 was approximately 6.6 per 1000 person-years of service, and 17% of Army veterans returning from Iraq or Afghanistan reported having sustained concussions, with more than half reporting two or more sustained concussions.

N-acetylcysteine (NAC) is synthetic small-molecule and a precursor of L-cysteine that results in glutathione elevation biosynthesis. NAC is a powerful antioxidant that acts directly as a scavenger of free radicals, for example, oxygen free radicals. NAC has a range of pleotropic salutary effects on acute and chronic CNS disorders through a variety of biochemical and pharmacological mechanisms of action, including quenching of reactive oxygen species (ROS), chelation of oxidative reactive metal ions, anti-inflammation, and neuromodulation via the cystine-glutamate antiporter. NAC can also increase the concentration and bioavailability of the endogenous antioxidant glutathione (GSH), anti-excitotoxic activity, and heavy metal-chelating activity.

GSH is the primary endogenous antioxidant and source of neuromodulatory cysteine in the brain. Traumatic brain injury (TBI) is associated with a post-concussive neurometabolic cascade involving injurious depletion of GSH. Decreased antioxidant reserve or GSH depletion in the brain can invoke a wide range of acute and chromic disorders of the CNS.

Intranasal (IN) delivery of drugs can target localized nasopharyngeal conditions or promote more distant drug distribution via the systemic circulation or by direct N2B entry into the brain. IN delivery for most localized conditions and for distant targeting require specialized delivery devices, various excipient agents, or formulations to enhance drug exposure to the nasal mucous membrane. The specialized delivery devices, excipient agents, or formulations prolong drug residency time on the nasal mucosal surface by enhancing drug penetration through the intervening superficial nasal mucus and mucosal layers.

In some embodiments, NAC can be employed as a chemical SH-containing reagent to thiolate chitosan by covalently conjugating NAC to chitosan. In some embodiments, the thiolated chitosan-NAC conjugate can be used as an excipient to promote experimentally IN delivery of insulin to the brain. In some embodiments, GSH can be employed as a chemical SH-containing reagent to thiolate chitosan by covalently conjugating GSH to chitosan. In some embodiments, the thiolated chitosan-GSH conjugate can be used as an excipient to experimentally promote IN delivery of insulin to the brain.

Independent of NAC or GSH's ability to form SH-containing adducts with compounds such as chitosan, NAC and GSH have independent direct pharmaceutical mucolytic properties through direct interactions with mucin, NAC, and GSH. As a mucolytic, administration of NAC or GSH in liquid form as a nasal spray can increase nasal clearance of a concomitantly administered compound, saccharin, by: 1) reducing the viscosity of the nasal mucus; and 2) enhancing the rate at which the mucus layer and adherent saccharin is removed from the nasal cavity by ciliary movement of the mucus layer into the throat.

The ability of NAC, NACA, a NAC metabolite, NAC congener, or D-NAC, or a pharmaceutically-acceptable salt of any of the foregoing containing active unconjugated SH groups to enhance mucociliary clearance result from a reduction in disulfide bonds between and within mucin molecules. The reduction in disulfide bonds between and within mucin molecules lowers the viscosity of the mucus layer.

However, NAC is <10% orally bioavailable and can have poor delivery across the BBB. N2B delivery of NAC may be pharmacodynamically advantageous in treating CNS disorders, and formulations to effectively administer and transit NAC to the brain are necessary to improve the therapeutic use of NAC. Disclosed herein are muco-adhesive in situ solubilized gel (sol-gel) formulations that can be used for N2B drug delivery. In some embodiments, a temperature-sensitive sol-gel phase transformation can provide direct device-based liquid-phase nasal instillation of a formulation at room temperature. An in situ gel formulation of the disclosure allows a rapid solid-phase transition of a formulation upon contact with the body-temperature nasal mucosa. In some embodiments, an in situ pharmaceutical composition of the disclosure can promote prolonged retention of the delivered drug on the inner surface of the nasal cavity. In some embodiments, an in situ pharmaceutical composition of the disclosure can deliver a compound N2B over an extended period of time. In some embodiments, an in situ pharmaceutical composition of the disclosure can deliver a compound for sustained delivery over a period of time.

In some embodiments, a pharmaceutical composition of the disclosure can be administered intranasally to treat a condition. In some embodiments, IN N2B administration of a pharmaceutical composition can be used to treat a CNS disorder. In some embodiments, the CNS disorder is mild traumatic brain injury. In some embodiments, the CNS disorder is Parkinson's disease. In some embodiments, the CNS disorder is brain cancer. In some embodiments, disclosed herein is a pharmaceutical composition comprising:

a) a glutathione precursor; b) a thermoresponsive polymer; and c) a viscosity modifying agent. In some embodiments, disclosed herein is a method of treating a condition, the method comprising administering a therapeutically-effective amount of a pharmaceutical composition to a subject, the pharmaceutical composition comprising: a) a glutathione precursor; and b) a thermoresponsive polymer, wherein the administering is intranasal.

In some embodiments, disclosed herein is a method of treating a condition, the method comprising administering a therapeutically-effective amount of a pharmaceutical composition to a subject in need thereof, the pharmaceutical composition comprising: a) a glutathione precursor; b) a thermoresponsive polymer; and c) a viscosity modifying agent.

In some embodiments, disclosed herein is a method of treating a condition, the method comprising administering a therapeutically-effective amount of a pharmaceutical composition to a subject in need thereof, the pharmaceutical composition comprising: a) a glutathione precursor; and b) a thermoresponsive polymer, wherein the condition is a central nervous system condition.

In some embodiments, disclosed herein is a method of treating a condition, the method comprising administering a therapeutically-effective amount of a pharmaceutical composition to a subject in need thereof, the pharmaceutical composition comprising: a) a glutathione precursor; and b) a thermoresponsive polymer, wherein the condition is a head condition.

In some embodiments, disclosed herein is a method of treating a condition, the method comprising administering a therapeutically-effective amount of a pharmaceutical composition to a human subject in need thereof, the pharmaceutical composition comprising: a) a glutathione precursor; and b) a thermoresponsive polymer.

Mechanism of Action

In some embodiments, a compound of the disclosure is a glutathione precursor. In some embodiments, a compound of the disclosure is a 5-lipogenase-activating protein (FLAP) inhibitor. In some embodiments, the glutathione precursor is NAC, NACA, a NAC metabolite, NAC congener, or D-NAC, or a pharmaceutically-acceptable salt thereof, and can act as a cysteine or GSH precursor. GSH is an endogenous compound that is essential to intracellular defenses against oxidative damage. GSH is a free radical scavenger and a key component of maintaining the redox state of cells in the CNS. GSH contains three amino acids: glutamate, glycine, and cysteine. Cysteine is present at the lowest concentration intracellularly. With oxidative stress, cysteine concentration is rate-limiting for the synthesis of GSH, which therefore becomes depleted because of concussion-induced excitotoxicity and the resultant changes in cell metabolism.

The major mechanism of action for NAC is the ability of NAC-derived cysteine to serve as a precursor for the synthesis and replenishment of cellular GSH stores. The strength of the effect of NAC on GSH concentration is controlled in part by the degree of endogenous cellular cysteine availability and the degree of endogenous GSH depletion. Correction of cellular GSH depletion is a major component of NAC's putative neuroprotective effects in psychiatric and neurodegenerative disorders. The neuroprotective effects of NAC depend on the extent to which NAC and/or NAC-derived reduced sulfhydryl equivalents can access the central nervous system to augment endogenous antioxidant activity.

NAC can also reduce disulfide bonds in proteins and disrupt ligand bonding and alter protein structures. NAC's ability to reduce disulfide bonds in mucolytic proteins accounts for the action of NAC as an effective mucolytic agent. NAC can also act as a glutamatergic modulator. Cysteine in the nervous system can assist in the regulation of neuronal intracellular and extracellular exchange of glutamate through the cystine-glutamate antiporter preferentially located on glial cells. In response to NAC-derived cystine, glial cells release glutamate into the extracellular space stimulating inhibitory metabotropic glutamate receptors on glutamatergic nerve terminals and thereby reducing the synaptic release of glutamate thereby affecting glutamatergic synaptic function and potentially ameliorating post-injury neuro-excitotoxicity.

NAC can act as a free radical scavenger and directly quench free radicals such as hydroxyl, nitrogen dioxide, carbonate and thiyl radicals and detoxify semiquinones, hypochlorous acid, and nitrosyl hydride. Under physiological conditions NAC does not react with nitric oxide, superoxide, hydrogen peroxide or peroxynitrite. NAC can act as an anti-inflammatory agent. NAC has demonstrated immunomodulatory activity in a variety of experimental and clinical pro-inflammatory conditions, including human autoimmune disorders such as Sjogren's syndrome and systemic lupus erythematosus.

Chitosan is a mucoadhesive that works by providing an ionic interaction between cationic amino groups and anionic sialic and sulfonic acid moieties of mucin. Chitosan also enhances mucosal permeabilization by opening epithelial tight junctions. Chemically modified chitosan-containing active sulfhydryl (SH) adducts (thiolation) can promote stronger muco-adhesion through formation of covalent disulfide bonds between the thiolated chitosan and the SH groups of mucins. In some embodiments, a formulation of the disclosure can comprise Poloxamer-407 as a thermo-responsive polymer, chitosan as a mucoadhesive polymer and permeation enhancer, and hydroxy-propyl methyl cellulose as an agent to provide added mechanical strength.

Administration of a sol-gel chitosan-containing mucoadhesive formulation to increase nasal drug bioavailability in combination with a compound of the disclosure can result in improved drug efficacy. In some embodiments, a compound of the disclosure can be added in solution or as a suspension to a chitosan-containing pharmaceutical composition, which can then be delivered in liquid form by an appropriate device. In some embodiments, the formulation can be delivered to a region or regions of the nasal cavity wherein ciliary-driven mucus clearance is not a significant contributor to drug clearance, such as the olfactory region of the upper portion of the human nasal cavity. In some embodiments, the compound of the disclosure is NAC, NAC amide (NACA), NAC derivative, NAC metabolite, NAC congener, a NAC dendrimer (D-NAC), GSH, GSH derivative, or a similar SH-containing compound.

Olfactory nasal cilia are specialized for odorant detection rather than mucus-layer motility. The 9+2 microtubular structures of olfactory nasal cilia lack dynein arms necessary for movement and are thus rendered immotile. Accordingly, NAC or GSH's mucolytic effect would not be expected to accelerate ciliary-dependent mucus clearance if deposition were confined to the olfactory region without motile cilia. In some embodiments, a compound of the disclosure can reduce disulfide bonds within and/or between proteins within the mucus layer. In some embodiments, a compound of the disclosure can reduce mucus viscosity and improve exposure of active ingredients contained within the formulation to the epithelial surface. In some embodiments, a compound of the disclosure can expose existing SH groups on the membrane surface for interaction with mucoadhesive groups on chitosan.

In some embodiments, the compound of the disclosure is NAC, NAC amide (NACA), NAC derivative, NAC metabolite, NAC congener, a NAC dendrimer (D-NAC), GSH, GSH derivative, or a similar SH-containing compound. In some embodiments, a compound of the disclosure can cleave disulfide groups within the mucus layer and create more SH groups to interact with chitosan. In some embodiments, the extent to which the addition of soluble or particulates of a compound of the disclosure within the formulation compete or interfere with the covalent-bond-based mucoadhesive properties of thiolated chitosan are determined experimentally.

In some embodiments, a formulation of the disclosure can prolong nasal residency time of NAC, NAC amide (NACA), NAC derivative, NAC metabolite, NAC congener, a NAC dendrimer (D-NAC), GSH, GSH derivative, or a similar SH-containing compound. In some embodiments, a formulation of the disclosure can promote enhanced permeation of a compound of the disclosure through the nasal mucosal layer. In some embodiments, a formulation of the disclosure can overcome the short residency time of a compound of the disclosure within the nasal cavity. In some embodiments, a formulation of the disclosure can improve uptake of a compound of the disclosure through the nasal mucosa. In some embodiments, a formulation of the disclosure can remove time-dependent loss of effect on increasing brain the concentration of a neurometabolite of a compound of the disclosure.

Compounds of the Invention

NAC is a glutathione prodrug that is used to treat acetaminophen-induced liver failure and to loosen thick mucus individuals with cystic fibrosis or chronic obstructive pulmonary disease. NAC can be taken intravenously, by mouth, or inhaled as a mist. Common side effects of NAC include nausea and vomiting when NAC is administered orally. NAC can also cause skin redness and itching and a non-immune type of anaphylaxis. NAC has multiple putative targets of action, and NAC has poor penetration into the CNS. NAC has been reported to cause nausea and vomiting, induce bronchospasm, slow blood clotting, and induce neurotoxicity in a dose-dependent manner. These issues can be problematic for patients with hemorrhagic stroke.

The present disclosure describes the use of at least one compound or a pharmaceutically-acceptable salt thereof to treat a condition. In some embodiments, the compound is NAC, NAC amide (NACA), NAC derivative, NAC metabolite, NAC congener, or NAC dendrimer (D-NAC), GSH, a GSH derivative, or a pharmaceutically-acceptable salt thereof. In some embodiments, the compound is a NAC prodrug or a pharmaceutically-acceptable slat thereof. In some embodiments, the compounds is NAC. In some embodiments, the compound is a NAC derivative. In some embodiments, the NAC derivative is GSH.

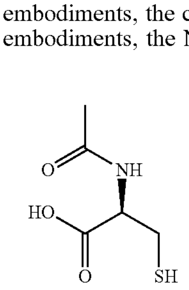
N-Acetylcysteine

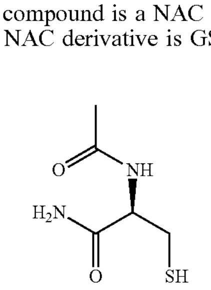
N-Acetylcysteine amide

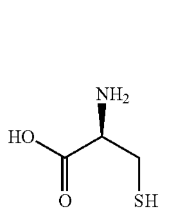
Cysteine

In some embodiments, the compound is a NAC dendrimer. D-NAC is a dendrimer conjugate where NAC is covalently bound to the surface of a dendrimer by disulfide linkages. In some embodiments, D-NAC comprises a polyamidoamine (PAMAM) hydroxyl dendrimer. In some embodiments, D-NAC comprises a polyglycerol sulfate dendrimer. In some embodiments, D-NAC comprises a polyamine dendrimer. In some embodiments, D-NAC comprises a polyamide dendrimer. In some embodiments, D-NAC comprises a linker. In some embodiments, GABA comprises a gamma-aminobutyric acid (GABA) linker. In some embodiments, D-NAC comprises a succinimidyl 3-(2-pyridyldithio)propionate (SPDP) linker.

In some embodiments, D-NAC has the formula:

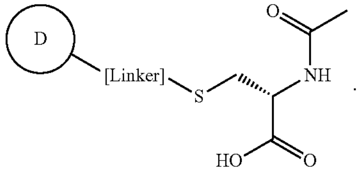

In some embodiments, D-NAC has the formula:

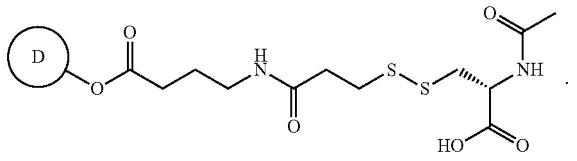

In some embodiments, the compound of the disclosure is a compound used to treat a CNS disease. In some embodiments, the compound is a compound to treat Parkinson's disease, for example, carbidopa, levodopa, a dopamine agonist, an MAO B inhibitor, a catechol O-methyltransferase (COMT) inhibitor, an anticholinergic, or amantadine. In some embodiments, the compound is carbodopa. In some embodiments, the compound is levodopa. In some embodiments, the dopamine agonist is pramipexole, ropinirole, rotigotine, or apomorphine. In some embodiments, the MAO B inhibitor is selegiline, rasagiline, or safinamide. In some embodiments, the COMT inhibitor is entacapone or tolcapone. In some embodiments, the anticholinergic agent is benztropine or trihexyphenidyl.

In some embodiments, the compound of the disclosure is a compound to treat Alzheimer's disease. In some embodiments, the compound is a cholinesterase inhibitor. In some embodiments, the cholinesterase inhibitor is donepezil, galantamine, or rivastigmine. In some embodiments, the compound is memantine.

Purity of Compounds of the Invention

Any compound of the disclosure can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Method of Detection and Clinical Assessment Tools

Magnetic resonance spectroscopy (MRS) is a technique associated with magnetic resonance imaging (MRI). MRS, also known as nuclear magnetic resonance (NMR) spectroscopy, is a non-invasive, ionizing-radiation-free analytical technique that can detect and measure metabolic changes in an organ, for example, the brain. MRS acquires signals from hydrogen protons in water and fat, which are approximately a thousand times more abundant than the molecules detected with MRS. In some embodiments, MRS is used to acquire a signal from a single localized region of the brain, referred to as a "voxel". In some embodiments, MRS can be used to determine a relative concentration of a biochemical in the region of the brain. In some embodiments, MRS can be used to determine a physical property of a region of the brain.

In some embodiments, MRS can be used to determine a relative concentration of a metabolite in the region of the brain. In some embodiments, the methods of the disclosure measure the concentration of a neurometabolic marker after IN N2B administration of NAC, NACA, NAC derivative, NAC metabolite, NAC congener, D-NAC, GSH, a GSH derivative, or a pharmaceutically-acceptable salt thereof. In some embodiments, the methods of the disclosure measure a concentration of GSH after IN N2B administration of NAC. In some embodiments, the methods of the disclosure measure a concentration change of GSH after IN N2B administration of NAC.

Also disclosed herein are methods of treating a brain disorder by monitoring absorption of a compound of the disclosure. In some embodiments, NAC, NACA, NAC derivative, NAC metabolite, NAC congener, D-NAC, GSH, a GSH derivative, or a pharmaceutically-acceptable salt thereof is administered to a subject, and dosing of NAC, NACA, NAC derivative, NAC metabolite, NAC congener, or D-NAC, or a pharmaceutically-acceptable salt thereof is changed based on MRS analysis of the brain to determine the concentration of a neurometabolite after IN N2B administration of NAC, NACA, NAC derivative, NAC metabolite, NAC congener, or D-NAC, or a pharmaceutically-acceptable salt thereof. In some embodiments, the NAC derivative is GSH.

In some embodiments, the neurometabolic marker is a NAC or GSH neurometabolite. In some embodiments, the neurometabolite is N-acetyl aspartate, lactate, glutamate, gamma-aminobutyric acid, or glutathione. In some embodiments, the NAC or GSH neurometabolite is glutathione. In some embodiments, the NAC or GSH neurometabolite is N-acetyl aspartate, or a compound whose MRS signal is identical or similar to N-acetyl aspartate.

In some embodiments, the methods of the disclosure can detect the action of NAC, NACA, NAC derivative, NAC metabolite, NAC congener, D-NAC, GSH, a GSH derivative, or a pharmaceutically-acceptable salt thereof as a cysteine precursor. In some embodiments, the NAC, NACA, NAC derivative, NAC metabolite, NAC congener, D-NAC, GSH, a GSH derivative, or a pharmaceutically-acceptable salt thereof can increase GSH synthesis. In some embodiments, the NAC, NACA, NAC derivative, NAC metabolite, NAC congener, or D-NAC, or a pharmaceutically-acceptable salt thereof can modulate gamma-aminobutyric acid (GABA) neurotransmission. In some embodiments, the action of NAC, NACA, NAC derivative, NAC metabolite, NAC congener, or D-NAC, or a pharmaceutically-acceptable salt thereof as cysteine precursors can be assessed by measuring a change in GSH by quantifying a $\beta$-$CH_2$ MRS signature from cysteine moieties.

The methods of the disclosure can further comprise Meshcher-Garwood Point Resolved Spectroscopy (MEGA-PRESS). In some embodiments, the methods of the disclosure can use MEGA-PRESS to separately but simultaneously measure post-drug administration changes in the $\beta$-CH2 MRS signature common to both NAC and GSH. In some embodiments, the methods of the disclosure can use MEGA-PRESS to determine the relative post-dose increase in $\beta$-CH2 MRS signature. In some embodiments, the methods of the disclosure can use MEGA-PRESS to determine the conversion of NAC, NACA, NAC derivative, NAC metabolite, NAC congener, D-NAC, GSH, a GSH derivative, or a pharmaceutically-acceptable salt thereof to NAC-metabolite in a region-specific fashion. In some embodiments, the methods of the disclosure can use MEGA-PRESS to determine the conversion of NAC, NACA, NAC derivative, NAC metabolite, NAC congener, D-NAC, or a GSH derivative, or a pharmaceutically-acceptable salt thereof to GSH in a region-specific fashion. In some embodiments, the methods of the disclosure can use MEGA-PRESS to determine the conversion of NAC, NACA, NAC derivative, NAC metabolite, NAC congener, D-NAC, or a GSH-derivative, or a pharmaceutically-acceptable salt thereof to GSH in a time-specific fashion.

In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize at least on delivery parameter of administering NAC, NACA, NAC derivative, NAC metabolite, NAC congener, D-NAC, GSH, a GSH derivative, or a pharmaceutically-acceptable salt thereof. In some embodiments, the delivery parameter is dose. In some embodiments, the delivery parameter is dose interval. In some embodiments, the delivery parameter is a dose delivery system.

In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize the presence of NAC in the brain. In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize the presence of GSH in the brain. In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize the presence of NAC and GSH in the brain.

In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize the presence of NAC in a region of the brain. In some embodiments, the methods of the disclosure detect and quantify a concentration change in a NAC-neurometabolite after administration of NAC, NACA, NAC derivative, NAC metabolite, NAC congener, or D-NAC, GSH, a GSH derivative, a pharmaceutically-acceptable salt thereof to optimize the presence of GSH in a region of the brain. In some embodiments, the methods of the disclosure detect and quantify a concentration change in a NAC-neurometabolite after administration of NAC, NACA, NAC derivative, NAC metabolite, NAC congener, D-NAC, GSH, a GSH derivative, or a pharmaceutically-acceptable salt thereof to optimize the presence of NAC and GSH in a region of the brain.

In some embodiments, a method of disclosure can detect and quantify a concentration change or rate of concentration change of a molecule. In some embodiments, the molecule is implicated in the pathogenesis or manifestations of a CNS disorder following administration of NAC, NACA, NAC derivative, NAC metabolite, NAC congener, or D-NAC, GSH, a GSH derivative, a pharmaceutically-acceptable salt thereof, or a pharmaceutical agent to treat a CNS disorder. In some embodiments, a method of the disclosure can detect or quantify a concentration change or rate of concentration change of a molecule to optimize the pharmacodynamic effect of the molecule one or more regions of the brain. In some embodiments, the molecule is a neurotransmitter, wherein the amount of the neurotransmitter in the brain is affected by a disease or condition. In some embodiments, the molecule is a neurotransmitter, wherein the change in concentration of the neurotransmitter affects a disease prognosis, progression, or manifestation. In some embodiments, the neurotransmitter is indoleamine, catecholamine, choline, amino acid, peptide, gaseous, lipid, or another neurotransmitter chemical class. In some embodiments, the neurotransmitter is quantified sing positron emission tomography, single-photon emission computerized tomography, fast-scan cyclic voltammetry, differential pulse voltammetry, microdialysis, fluorescence imaging, magnetic resonance spectroscopy, or a biosensor.

In some embodiments, a method of the disclosure can detect and quantify a change in a cellular function or perturbation implicated in the pathogenesis or manifestations of a CNS disorder following administration of NAC, NACA, NAC derivative, NAC metabolite, NAC congener, or D-NAC, GSH, a GSH derivative, a pharmaceutically-acceptable salt thereof, or a pharmaceutical agent to treat a CNS disorder. In some embodiments, a method of the disclosure can detect and quantify a change in a cellular function or perturbation implicated in the pathogenesis or manifestations of a CNS disorder to optimize the pharmacodynamic effect of administering a compound. In some embodiments, the perturbation is cellular depletion, proliferation, activation, deactivation, neural net connectivity, or loss of neural net connectivity. In some embodiments, the perturbation is a measured change in a parameter of a disease-relevant physiological brain function, for example, glymphatic flow or blood flow.

The methods of the disclosure can further comprise obtaining biological samples for analysis. In some embodiments, the method further comprises quantifying an amount of free NAC in a plasma sample. In some embodiments, the method further comprises quantifying an amount of total NAC in a plasma sample. In some embodiments, the method further comprises quantifying an amount of plasma GSH. In some embodiments, the method further comprises quantifying a ratio of reduced GSH to oxidized GSH (GSH/GSSG). In some embodiments, the method further comprises quantifying an amount of NAC or a NAC metabolite in a cerebrospinal fluid sample.

Several tools can be utilized to diagnose and assess the clinical and neuropsychological features of a brain condition, for example, mild traumatic brain injury. In some embodiments, standard physical and neurological examinations, and neuropsychometric batteries and scales with broader applicability (e.g., Glasgow coma scale) can be used to diagnose and assess a subject with a CNS condition.

Post-concussion symptom score (PCSS): The PCSS score consists of 22 items that evaluate symptoms on a 7-point scale. 0 correlates to no symptoms, and 6 correlates to severe symptoms. PCSS scores have utility for subjects ages 11 and above in identifying individuals with clinically-diagnosed concussion, and in predicting prolonged recovery. PCSS scores have also demonstrated test-retest reliability.

Graded symptom checklist (GSC): The GSC consists of 16 items scored on a 7-point scale. The GSC scale is applicable to subjects ages 13 and above, and incorporates a three-factor structure (cognitive, somatic, and neurobehavioral). The GSC scale has demonstrated internal validity, test-retest reliability, and convergent validity with respect to balance and cognitive performance.

Standardized concussion assessment tool (SCAT): SCAT is a standardized tool that is used by healthcare professionals, and incorporates other assessment scales, such as GCS, Maddocks questions for memory assessment, PCSS, and other neurological and cognitive tests.

Immediate post-concussion assessment and cognitive testing (ImPACT): ImPACT is a computerized test battery with 3 components, such as demographic data, neuropsychological testing, and PCSS. ImPACT has the advantage of including assessments of cognition (e.g., attention, processing speed, impulsivity, and reaction time). In a combination with a scale for mTBI symptoms, ImPACT has a sensitivity of 81.9%, and a specificity of 89.4%. ImPACT is not subject to substantial practice effects.

King-Devick Scale: The King-Devick scale is a brief test administered acutely following head injury in which the subject must read patterns of letters and numbers on test cards. The King-Devick scale assess language, attention, and eye movements, all of which can be impaired in a CNS condition, for example, concussion. The test-retest reliability of the King-Devick scale over a period of 1-2 years compares is comparable to other standard assessment methods.

Biomarkers and imaging: Electrophysiological techniques, imaging techniques, and blood tests can be used to assess the CNS condition of a subject. Event-related potentials (EPRs) can be used to evaluate computer-processed electroencephalogram (EEG) signals time-locked to a perpetual or cognitive task. In some embodiments, computed tomography (CT) and magnetic resonance imaging (MRI) can be used to diagnose or track the progress of a CNS condition. In some embodiments, the MRI is functional MRI. In some embodiments, diffusion tensor imaging can be used to diagnose or track the progression of a CNS condition. In some embodiments, other FDA-cleared devices can be used to quantify and track neurofunctional impairment resulting from mTBI, Parkinson's disease, or another CNS disease.

Methods of Administration

Compounds of the disclosure can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. In some embodiments, a therapeutically-effective amount of a compound of the disclosure can be administered intranasally.

A compound or pharmaceutical composition of the disclosure can be administered in a local manner, for example, intranasally. IN N2B administration is a route of administration where drugs are insufflated through the nose.

The nasal cavity's easily accessible, rich vascular plexus permits topically administered drugs to achieve therapeutically effective blood levels rapidly while avoiding intravenous catheters. In some embodiments, nasal administration can be used to deliver a compound of pharmaceutical composition of the disclosure to the blood stream. In some embodiments, nasal administration can be used to deliver a compound or pharmaceutical composition of the disclosure to the blood. In some embodiments, nasal administration delivers a compound or pharmaceutical composition of the disclosure to the blood, which then enters the brain. IN N2B administration of a compound or pharmaceutical composition disclosed herein avoids gastrointestinal destruction and hepatic first pass metabolism, which allows the compound or pharmaceutical composition to be most cost-effectively and rapidly bioavailable compared to oral administration. In some embodiments, IN N2B administration of a compound or pharmaceutical composition of the disclosure can make the bioavailability of the compound or pharmaceutical composition more predictable compared to oral administration.

In some embodiments, IN N2B administration of a compound or pharmaceutical composition of the disclosure can have a rate of absorption that is greater than that obtained by subcutaneous or intramuscular administration. In some embodiments, IN N2B administration of a compound or pharmaceutical composition of the disclosure can have a resulting plasma concentration that is greater than that obtained by subcutaneous or intramuscular administration.

In some embodiments, IN N2B administration of a compound or pharmaceutical composition of the disclosure can rapidly achieve therapeutic brain and spinal cord drug concentrations.

A liquid pharmaceutical composition of the disclosure can be administered to a subject intranasally using a device. In some embodiments, a liquid formulation can be delivered as drops with a pipette. In some embodiments, a liquid formulation can be delivered with a catheter and a squirt tube, for example, a rhinyl catheter and a squirt tube. In some embodiments, a liquid formulation can be delivered using a squeeze bottle.

In some embodiments, a liquid formulation can be administered intranasally using a mechanical spray pump. In some embodiments, a liquid formulation can be intranasally administered using a metered-dose spray pump. In some embodiments, a liquid formulation can be delivered using a single-dose or duo-dose spray device. In some embodiments, a liquid formulation can be delivered using a nasal pressurized metered-dose inhaler (pMDI).

In some embodiments, a liquid formulation can be administered intranasally using a gas-driven spray system or atomizer. In some embodiments, a liquid formulation can be administered intranasally using a nitrogen gas-driven system. In some embodiments, a liquid formulation can be administered intranasally using a powdered nebulizer or atomizer. In some embodiments, a liquid formulation can be administered intranasally using a VibrENT pulsation membrane nebulizer. In some embodiments, a liquid formulation can be administered intranasally using an Aeroneb Solo vibrating mesh nebulizer. In some embodiments, a liquid formulation can be administered intranasally using a ViaNase atomizer. In some embodiments, a liquid formulation can be administered intranasally using a Teleflex LMA® MAD Nasal™ mucosal atomization device. In some embodiments, a liquid formulation can be administered intranasally using a Aptar CPS 5-mL nasal pump.

In some embodiments, a powder formulation can be administered intranasally using a device. In some embodiments, a powder formulation can be administered intranasally using a nasal powder inhaler. In some embodiments, a powder formulation can be administered intranasally using a nasal powder sprayer. In some embodiments, a powder formulation can be administered intranasally using a nasal powder insufflator. In some embodiments, a powder formulation can be administered intranasally using a breath-powered Bi-Directional™ technology device.

The compounds or pharmaceutical compositions of the disclosure can be administered in various positions. In some embodiments, the compounds or pharmaceutical compositions of the disclosure can be administered to the subject in the supine position. In some embodiments, the compounds or pharmaceutical compositions of the disclosure can be administered to the subject in the seated position.

Pharmaceutical Compositions

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives. In some embodiments, pharmaceutical compositions of the disclosure can comprise a stabilizer. In some embodiments, the stabilizer is Captisol®, Monosteol™, Vivapur® MCG 591P, Vivapur® MCG 611P, Vivapur® MCG 811P, Neosorb sorbitol solution sweetener coating, HiCel MCG 581, HiCel MCG591, or HiCel MCG611.

In some embodiments, the pharmaceutical compositions of the disclosure can comprise an absorption enhancer. In some embodiments, the absorption enhancer is a peptide or a protein. In some embodiments, the absorption enhancer is calcitonin, desmopressin, insulin, leuprolide, or octreotide. In some embodiments, the absorption enhancer is a non-peptide macromolecule. In some embodiments, the absorption enhancer is heparin, low-molecular weight heparin, enoxaparin, fondaparinux, an oligonucleotide, or vancomycin. In some embodiments, the absorption enhancer is a hydrophilic small molecule. In some embodiments, the absorption enhancer is an aminoglycoside, amikacin, gentamycin, amphotericin B, or bisphosphonate.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A pharmaceutical composition of the disclosure can comprise N-acetylcysteine (NAC), NAC amide, a NAC derivative, or a NAC metabolite. In some embodiments, the pharmaceutical composition comprises NAC. In some embodiments, the pharmaceutical composition comprises NAC amide. In some embodiments, the pharmaceutical composition comprises a NAC derivative. In some embodiments, the pharmaceutical composition comprises a NAC metabolite. In some embodiments, the NAC metabolite is glutathione.

In some embodiments, a pharmaceutical composition of the disclosure can comprise from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, or from about 65% to about 70% of a compound of the disclosure. In some embodiments, a pharmaceutical composition of the disclosure can comprise about 5%, about 10%, about 15%, about 20%, about 25%, about 30%, about 35%, about 40%, about 45%, about 50%, about 55%, about 60%, about 65%, or about 70% of a compound of the disclosure. In some embodiments, a pharmaceutical composition of the disclosure can comprise about 10%, about 11%, about 12%, about 13%, about 14%, about 15%, about 16%, about 17%, about 18%, about 19%, or about 20% of a compound of the disclosure. In some embodiments, a pharmaceutical composition of the disclosure can comprise about 10% of a compound of the disclosure. In some embodiments, a pharmaceutical composition of the disclosure can comprise about 15% of a compound of the disclosure. In some embodiments, a pharmaceutical composition of the disclosure can comprise about 17% of a compound of the disclosure. In some embodiments, a pharmaceutical composition of the disclosure can comprise about 20% of a compound of the disclosure. In some embodiments, a pharmaceutical composition of the disclosure can comprise about 25% of a compound of the disclosure. In some embodiments, a pharmaceutical composition of the disclosure can comprise about 30% of a compound of the disclosure.

A pharmaceutical composition of the disclosure can be in the form of a solubilized gelling (sol-gel) solution. In some embodiments, the pharmaceutical composition can comprise a thermoresponsive polymeric gelling agent that is administered in liquid form. In some embodiments, the pharmaceutical composition comprising a thermoresponsive polymeric gelling agent can undergo in situ gelation, resulting in mucoadhesion and sustained drug delivery. In some embodiments, a pharmaceutical composition of the disclosure can comprise from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 95%, or from about 65% to about 70% of a compound of the disclosure in a sol-gel solution. In some embodiments, a pharmaceutical composition of the disclosure can comprise about 5%, about 10%, about 15%, about 20%, about 25%, about 30%, about 35%, about 40%, about 45%, about 50%, about 55%, about 60%, about 65%, or about 70% of a compound of the disclosure in a sol-gel solution. In some embodiments, a pharmaceutical composition of the disclosure can comprise about 10%, about 11%, about 12%, about 13%, about 14%, about 15%, about 16%, about 17%, about 18%, about 19%, or about 20% of a compound of the disclosure in a sol-gel solution. In some embodiments, a pharmaceutical composition of the disclosure can comprise about 15% of a compound of the disclosure in a sol-gel solution. In some embodiments, a pharmaceutical composition of the disclosure can comprise about 16% of a compound of the disclosure in a sol-gel solution. In some embodiments, a pharmaceutical composition of the disclosure can comprise about 17% of a compound of the disclosure in a sol-gel solution. In some embodiments, a pharmaceutical composition of the disclosure can comprise about 15% of NAC, NAC amide, a NAC derivative, NAC congener, D-NAC, GSH, GSH derivative, or a pharmaceutically acceptable salt thereof in a sol-gel solution. In some embodiments, a pharmaceutical composition of the disclosure can comprise about 16% of NAC, NAC amide, a NAC derivative, NAC congener, D-NAC, GSH, GSH derivative, or a pharmaceutically acceptable salt thereof in a sol-gel solution. In some embodiments, a pharmaceutical composition of the disclosure can comprise about 17% of NAC, NAC amide, a NAC derivative, NAC congener, D-NAC, GSH, GSH derivative, or a pharmaceutically acceptable salt thereof in a sol-gel solution.

A pharmaceutical composition of the disclosure can further comprise at least one excipient. In some embodiments, a pharmaceutical composition of the disclosure comprises a thermoresponsive polymer. In some embodiments, a pharmaceutical composition of the disclosure comprises a polymeric gelling agent. In some embodiments, the thermoresponsive polymer is a poloxamer. In some embodiments, the thermoresponsive polymer is poloxamer 407. In some embodiments, the thermoresponsive polymer is poloxamer 338.

In some embodiments, the thermoresponsive polymer is present in the pharmaceutical composition in an amount of from about 5% to about 30%. In some embodiments, the thermoresponsive polymer is present in the pharmaceutical composition in an amount of from about 5% to about 10%, from about 10% to about 15%, from about 15% to about 20%, from about 20% to about 25%, or from about 25% to about 30%. In some embodiments, the thermoresponsive polymer is present in the pharmaceutical composition in an amount of about 5%, about 10%, about 15%, about 20%, about 25%, or about 30%. In some embodiments, the thermoresponsive polymer is present in the pharmaceutical composition in an amount of about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20%. In some embodiments, the thermoresponsive polymer is present in the pharmaceutical composition in an amount of about 10%. In some embodiments, the thermoresponsive polymer is present in the pharmaceutical composition in an amount of about 11%. In some embodiments, the thermoresponsive polymer is present in the pharmaceutical composition in an amount of about 12%. In some embodiments, the thermoresponsive polymer is present in the pharmaceutical composition in an amount of about 13%. In some embodiments, the thermoresponsive polymer is present in the pharmaceutical composition in an amount of about 14%. In some embodiments, the thermoresponsive polymer is present in the pharmaceutical composition in an amount of about 15%.

In some embodiments, a pharmaceutical composition of the disclosure comprises a viscosity modifying agent. In some embodiments, the viscosity modifying agent is a polymer. In some embodiments, the viscosity modifying agent is a poloxamer. In some embodiments, the viscosity modifying agent is poloxamer 188. In some embodiments, the viscosity modifying agent is poloxamer 237.

In some embodiments, the viscosity modifying agent is present in the pharmaceutical composition in an amount of from about 1.5% to about 10%. In some embodiments, the viscosity modifying agent is present in the pharmaceutical composition in an amount of from about 1.5% to about 2%, from about 2% to about 2.5%, from about 2.5% to about 3%, from about 3% to about 3.5%, from about 3.5% to about 4%, from about 4% to about 4.5%, from about 4.5% to about 5%, from about 5% to about 5.5%, from about 5.5% to about 6%, from about 6% to about 6.5%, from about 6.5% to about 7%, from about 7% to about 7.5%, from about 7.5% to about 8%, from about 8% to about 8.5%, from about 8.5% to about 9%, from about 9% to about 9.5%, or from about 9.5% to about 10%. In some embodiments, the viscosity modifying agent is present in the pharmaceutical composition in an amount of about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%. In some embodiments, the viscosity modifying agent is present in the pharmaceutical composition in an amount of about 2%. In some embodiments, the viscosity modifying agent is present in the pharmaceutical composition in an amount of about 2.5%. In some embodiments, the viscosity modifying agent is present in the pharmaceutical composition in an amount of about 2.8%. In some embodiments, the viscosity modifying agent is present in the pharmaceutical composition in an amount of about 3.0%. In some embodiments, the viscosity modifying agent is present in the pharmaceutical composition in an amount of about 3.5%. In some embodiments, the viscosity modifying agent is present in the pharmaceutical composition in an amount of about 3.8%.

In some embodiments, a pharmaceutical composition of the disclosure comprises a poloxamer that acts as a surfactant, emulsifying agent, solubilizing agent, dispersing agent, or an in vivo absorbance enhancer. In some embodiments, a pharmaceutical composition of the disclosure comprises poloxamer 68, poloxamer 88, poloxamer 98, poloxamer 108, poloxamer 124, poloxamer 188, poloxamer 237, poloxamer 338, or poloxamer 407. In some embodiments, a pharmaceutical composition of the disclosure comprises poloxamer 407. In some embodiments, a pharmaceutical composition of the disclosure comprises poloxamer 188.

In some embodiments, a pharmaceutical composition of the disclosure can comprise an agent that increases the mechanical strength of the formulation. In some embodiments, the mucoadhesive agent is a cellulose. In some embodiments, the mucoadhesive agent is methylcellulose. In some embodiments, the mucoadhesive agent is hydroxypropyl methylcellulose.

In some embodiments, the mucoadhesive agent is present in the pharmaceutical composition in an amount of from about 0.1% to about 0.5%. In some embodiments, the mucoadhesive agent is present in the pharmaceutical composition in an amount of from about 0.1%, to about 0.2%, from about 0.2% to about 0.3%, from about 0.3% to about 0.4%, or from about 0.4% to about 0.5%. In some embodiments, the mucoadhesive agent is present in the pharmaceutical composition in an amount of about 0.1%, about 0.2%, about 0.3%, about 0.4%, about 0.5%. In some embodiments, the mucoadhesive agent is present in the pharmaceutical composition in an amount of about 0.1%. In some embodiments, the mucoadhesive agent is present in the pharmaceutical composition in an amount of about 0.2%. In some embodiments, the mucoadhesive agent is present in the pharmaceutical composition in an amount of about 0.3%. In some embodiments, the mucoadhesive agent is present in the pharmaceutical composition in an amount of about 0.4%. In some embodiments, the mucoadhesive agent is present in the pharmaceutical composition in an amount of about 0.5%.

In some embodiments, a pharmaceutical composition of the disclosure comprises a preservative. In some embodiments, the preservative is a paraben. In some embodiments, the preservative is methyl paraben. In some embodiments, a pharmaceutical composition of the disclosure comprises a combination of two or more preservatives. In some embodiments, a pharmaceutical composition of the disclosure comprises two preservatives. a pharmaceutical composition of the disclosure comprises three preservatives. a pharmaceutical composition of the disclosure comprises four preservatives. a pharmaceutical composition of the disclosure comprises a combination of two more parabens, for example, a combination of two or more of methyl paraben, propyl paraben, and butyl paraben.

In some embodiments, the preservative is present in the pharmaceutical composition in an amount of from about 0.1% to about 0.5%. In some embodiments, the preservative is present in the pharmaceutical composition in an amount of from about 0.1% to about 0.2%, from about 0.2% to about 0.3%, from about 0.3% to about 0.4%, or from about 0.4% to about 0.5%. In some embodiments, the preservative is present in the pharmaceutical composition in an amount of about 0.1%, about 0.2%, about 0.3%, about 0.4%, or about 0.5%. In some embodiments, the preservative is present in the pharmaceutical composition in an amount of about 0.1%. In some embodiments, the preservative is present in the pharmaceutical composition in an amount of about 0.2%. In some embodiments, the preservative is present in the pharmaceutical composition in an amount of about 0.3%. In some embodiments, the preservative is present in the pharmaceutical composition in an amount of about 0.4%. In some embodiments, the preservative is present in the pharmaceutical composition in an amount of about 0.5%.

In some embodiments, a pharmaceutical composition of the disclosure is formulated for intranasal administration. In some embodiments, a pharmaceutical composition of the disclosure is formulated as a gel. In some embodiments, a pharmaceutical composition of the disclosure is formulated as a solution.

A pharmaceutical composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 h. In some embodiments, a pharmaceutical composition of the disclosure can delay the release of an effective dose of a compound of the disclosure, for example, for about 1, for about 2, for about 3, or for about 4 hours. In some embodiments, a pharmaceutical composition of the disclosure can delay the release of an effective dose of a compound of the disclosure, for example, for about 6, for about 8, for about 10, or for about 12 hours.

A controlled release formulation can be a sustained or extended release form. A sustained or extended release form can be formulated to sustain or extend, for example, the compound's action over an extended period of time. A sustained or extended release form can be formulated to provide an effective dose of any compound described herein (e.g., provide a physiologically-effective blood profile) over about 4, about 8, about 12, about 16 or about 24 h. In some embodiments, a pharmaceutical composition of the disclosure can provide sustained or extended delivery of an effective dose of a compound of the disclosure, for example, for about 1, for about 2, for about 3, or for about 4 hours. In some embodiments, a pharmaceutical composition of the disclosure can provide sustained or extended delivery of an effective dose of a compound of the disclosure, for example, for about 1, for about 2, for about 3, or for about 4 hours in a region of the brain. In some embodiments, a pharmaceutical composition of the disclosure can provide sustained or extended delivery of an effective dose of a compound of the disclosure, for example, for about 6, for about 8, for about 10, or for about 12 hours in a region of the brain Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

In some embodiments, a pharmaceutical composition of the disclosure can have a gelation temperature of from about 26° C. to about 29° C. In some embodiments, a pharmaceutical composition of the disclosure can have a gelation temperature of from about 26° C. to about 26.5° C., from about 26.5° C. to about 27° C., from about 27° C. to about 27.5° C., from about 27.5° C. to about 28° C., from about 28° C. to about 28.5° C., or from about 28.5° C. to about 29° C. In some embodiments, a pharmaceutical composition of the disclosure can have a gelation temperature of about 26° C., about 26.5° C., about 27° C., about 27.5° C., about 28° C., about 28.5° C., or about 29° C. In some embodiments, a pharmaceutical composition of the disclosure can have a gelation temperature of about 26° C. In some embodiments, a pharmaceutical composition of the disclosure can have a gelation temperature of about 26.5° C. In some embodiments, a pharmaceutical composition of the disclosure can have a gelation temperature of about 27° C. In some embodiments, a pharmaceutical composition of the disclosure can have a gelation temperature of about 27.5° C. In some embodiments, a pharmaceutical composition of the disclosure can have a gelation temperature of about 28° C.

In some embodiments, a pharmaceutical composition can have a gel strength at 34° C. of from about 7335 Pa to about 7465 Pa. In some embodiments, a pharmaceutical composition can have a gel strength at 34° C. of from about 7300 Pa to about 7325 Pa, from about 7325 Pa to about 7350 Pa, from about 7350 Pa to about 7375 Pa, from about 7375 Pa to about 7400 Pa, from about 7400 Pa to about 7425 Pa, from about 7425 Pa to about 7450 Pa, or from about 7450 Pa to about 7475 Pa. In some embodiments, a pharmaceutical composition can have a gel strength at 34° C. of about 7300 Pa, about 7325 Pa, about 7350 Pa, about 7375 Pa, about 7400 Pa, about 7425 Pa, about 7450 Pa, or about 7475 Pa. In some embodiments, a pharmaceutical composition can have a gel strength at 34° C. of about 7350 Pa. In some embodiments, a pharmaceutical composition can have a gel strength at 34° C. of about 7400 Pa. In some embodiments, a pharmaceutical composition can have a gel strength at 34° C. of about 7450 Pa.

In some embodiments, a pharmaceutical composition can have a viscosity at about 34° C. of from about 2 Pa·s to about 2.5 Pa·s. In some embodiments, a pharmaceutical composition can have a viscosity at about 34° C. of from about 2 Pa·s to about 2.1 Pa·s, from about 2.1 Pa·s to about 2.2 Pa·s, from about 2.2 Pa·s to about 2.3 Pa·s, from about 2.3 Pa·s to about 2.4 Pa·s, or from about 2.4 Pa·s to about 2.5 Pa·s. In some embodiments, a pharmaceutical composition can have a viscosity at about 34° C. of about 2 Pa·s, about 2.1 Pa·s, about 2.2 Pa·s, about 2.3 Pa·s, about 2.4 Pa·s, or about 2.5 Pa·s. In some embodiments, a pharmaceutical composition can have a viscosity at about 34° C. of about 2.1 Pa·s. In some embodiments, a pharmaceutical composition can have a viscosity at about 34° C. of about 2.2 Pa·s. In some embodiments, a pharmaceutical composition can have a viscosity at about 34° C. of about 2.3 Pa·s.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

A compound or pharmaceutical composition can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

A compound or pharmaceutical composition of the disclosure can be administered more than one time. In some embodiments, a compound or pharmaceutical composition of the disclosure can be administered once daily. In some embodiments, a compound or pharmaceutical composition of the disclosure can be administered twice daily. In some embodiments, a compound or pharmaceutical composition of the disclosure can be administered three times daily. In some embodiments, a compound or pharmaceutical composition of the disclosure can be administered, and the administration can be repeated at least once. In some embodiments, administration of a compound or a pharmaceutical composition can be repeated once. In some embodiments, administration of a compound or a pharmaceutical composition can be repeated twice. In some embodiments, administration of a compound or a pharmaceutical composition can be repeated three times.

In some embodiments, administration of a compound or a pharmaceutical composition can be repeated after about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days. In some embodiments, administration of a compound or pharmaceutical composition can be repeated after about 7 days. In some embodiments, administration of a compound or pharmaceutical composition can be repeated after about 14 days.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing

Compounds or pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass. A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some embodiments, a method of the disclosure administers a therapeutically-effective amount from about 100 mg to about 400 mg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg. In some embodiments, a compound described herein can be present in a composition in an amount of about 350 mg. In some embodiments, a compound described herein can be present in a composition in an amount of about 400 mg. Combination Therapy The compounds or pharmaceutical compositions of the disclosure can be administered with at least one additional therapeutic agent. In some embodiments, the compounds or pharmaceutical compositions of the disclosure can be administered with one additional therapeutic agent. In some embodiments, the compounds or pharmaceutical compositions of the disclosure can be administered with two additional therapeutic agents. In some embodiments, the compounds or pharmaceutical compositions of the disclosure can be administered with three additional therapeutic agents.

In some embodiments, the therapeutic agent is a FLAP inhibitor. In some embodiments, the FLAP inhibitor is MK-866 (L 663536), quiflapon (MK-591), fiboflapon (GSK2190915; AM-803), veliflapon (BAY X 1005; DG-031), AM679, or a pharmaceutically-acceptable salt thereof. In some embodiments, the therapeutic agent is glutathione. In some embodiments, the therapeutic agent is a glutathione-decorated nanoparticle.

In some embodiments, the therapeutic agent is a Cathepsin B inhibitor. In some embodiments, the Cathepsin B inhibitor is antipain dihydrochloride, CA-074, CA-074 methyl ester, Calpain inhibitor I, Calpain inhibitor II, chymostatin, cystatin, E-64, leupeptin trifluoroacetate salt, procathepsin B fragment, Z-Leu-Leu-Leu fluoromethyl ketone. In some embodiments, the Cathepsin B inhibitor is antipain dihydrochloride. In some embodiments, the Cathepsin B inhibitor is CA-074. In some embodiments, the Cathepsin B inhibitor is cystatin. In some embodiments, the Cathepsin B inhibitor is chymostatin.

In some embodiments, the therapeutic agent is a poly (ADP-ribose) polymerase (PARP) inhibitor. In some embodiments, the PARP inhibitor is olaparib, rucaparib, niraparib, talazoparib, veliparib, pamiparib, rucaparib, CEP 9722, E7016, Iniparib, or 3-aminobenzamide. In some embodiments, the PARP inhibitor is olaparib. In some embodiments, the PARP inhibitor is rucaparib. In some embodiments, the PARP inhibitor is niraparib. In some embodiments, the PARP inhibitor istalazoparib.

In some embodiments, the therapeutic agent is probenecid. In some embodiments, the therapeutic agent is phenserine. In some embodiments, the therapeutic agent is a dopaminergic agent.

Method of Treatment

In some embodiments, disclosed herein is a method of treating a condition, the method comprising administering a therapeutically-effective amount of a pharmaceutical composition to a subject, the pharmaceutical composition comprising: a) N-acetylcysteine (NAC), NAC amide, a NAC derivative, or a NAC metabolite; and b) a thermoresponsive polymer, wherein the administering is intranasal.

The present disclosure describes the use of a compound or pharmaceutical composition to treat a brain condition. In some embodiments, the brain condition is a neurological disorder. A neurological disorder is any disorder of the nervous system. Structural, biochemical, or electrical abnormalities in the brain, spinal cord, or other nerves can result in a range of symptoms. Examples of symptoms that arise from neurological disorders include paralysis, muscle weakness, poor coordination, loss of sensation, seizures, confusion, pain, and altered levels of consciousness. In some embodiments, the disclosure describes the use of a compound or pharmaceutical composition to treat brain damage, such as cerebral lobe (e.g., basal ganglia, cerebellum, or the brainstem) damage, frontal lobe damage, parietal lobe damage, temporal lobe damage, or occipital lobe damage. In some embodiments, the present disclosure describes the use of a compound or pharmaceutical composition to treat brain dysfunction according to type: aphasia (language), dysgraphia (writing), dysarthria (speech), apraxia (patterns of sequences of movements), agnosia (identifying things or people), or amnesia (memory). In some embodiments the present disclosure describes the use of a compound or pharmaceutical composition to treat spinal cord disorders, peripheral neuropathy and other peripheral nervous system disorders, cranial nerve disorders (e.g., Trigeminal neuralgia), autonomic nervous system disorders (e.g., dysautonomia, Multiple System Atrophy), or seizure disorders (e.g., epilepsy).

In some embodiments, the brain condition is a movement disorder of the central and peripheral nervous system, such as essential tremor, amyotrophic lateral sclerosis (ALS), Tourette's syndrome, multiple sclerosis, Parkinson's disease, myaligic encephalomyelitis, chronic fatigue syndrome, or peripheral neuropathy. In some embodiments, the movement disorder is Parkinson's disease. In some embodiments, the disclosure describes the use of a compound or pharmaceutical composition to treat sleep disorders (e.g., narcolepsy), migraines and other types of headaches, or central neuropathy. In some embodiments, the disclosure describes the use of a compound or pharmaceutical composition to treat a neuropsychiatric illness, such as attention deficit hyperactivity disorder, autism, or obsessive compulsive disorder.

In some embodiments, the brain condition is a CNS condition. CNS disorders are a group of neurological disorders that affect the structure or function of the brain or spinal cord, which collectively form the CNS. The disclosure describes use of a compound or pharmaceutical composition to treat a CNS disorder caused by traumatic brain injury, concussion, post-concussion syndrome, infections, degeneration (e.g., degenerative spinal disorders), structural defects (e.g., anencephaly, hypospadias, spina bifida, microgyria, polymicrogyria, bilateral frontoparietal polymicrogyria, or pachgyria), tumors, autoimmune disorders, or stroke. In some embodiments, the disclosure describes the use of a compound or pharmaceutical composition to treat traumatic brain injury. In some embodiments, the disclosure describes the use of a compound or pharmaceutical composition to treat subarachnoid hemorrhage. In some embodiments, the disclosure describes the use of a compound or pharmaceutical composition to treat concussion. In some embodiments, the disclosure describes the use of a compound or pharmaceutical composition to treat post-concussion syndrome. In some embodiments, the disclosure describes the use of a compound or pharmaceutical composition to treat chronic fatigue syndrome.

In some embodiments, the disclosure describes the use of a compound or pharmaceutical composition to treat stroke. Stroke is a medical condition in which poor blood flow to the brain results in cell death. The two main types of strokes are ischemic stroke resulting from a lack of blood flow, and hemorrhagic stroke resulting from bleeding. Signs and symptoms of a stroke may include an inability to move or feel on one side of the body, problems understanding or speaking, and a loss of vision to one side. In some embodiments, the disclosure describes the use of a compound or pharmaceutical composition to treat hemorrhagic stroke. In some embodiments, the disclosure describes the use of a compound or pharmaceutical composition to treat intracerebral hemorrhagic (ICH) stroke.

In some embodiments, a compound or pharmaceutical composition of the disclosure can be used to treat brain dysfunction. In some embodiments, a compound or pharmaceutical composition of the disclosure can be used to treat aphasia (language), dysgraphia (writing), dysarthria (speech), apraxia (patterns of sequences or movements), agnosia (identifying things or people), or amnesia (memory). In some embodiments, a compound or pharmaceutical composition of the disclosure can be used to treat a spinal cord disorder, peripheral neuropathy, a peripheral nervous system disorder, cranial nerve disorder, autonomic nervous system disorder, or a seizure disorder. In some embodiments, a compound or pharmaceutical composition of the disclosure can be used to treat a cranial nerve disorder, for example, trigeminal neuralgia. In some embodiments, a compound or pharmaceutical composition of the disclosure can be used to treat an autonomic nervous system disorder, for example, dysautonomia or multiple system atrophy. In some embodiments, a compound or pharmaceutical composition of the disclosure can be used to treat a seizure disorder, for example, epilepsy.

In some embodiments, the disclosure describes the use of a compound or pharmaceutical composition to treat brain cancer. In some embodiments, the brain cancer is an astrocytoma of the brain or spinal cord. In some embodiments, the brain cancer is a brain stem glioma. In some embodiments, the brain cancer is glioblastoma multiforme. In some embodiments, the brain cancer is meningioma. In some embodiments, the brain cancer is an ependymoma. In some embodiments, the brain cancer is an oligodendroglioma. In some embodiments, the brain cancer is a mixed glioma. In some embodiments, the brain cancer is a pituitary cancer. In some embodiments, the brain cancer is a craniopharyngioma. In some embodiments, the brain cancer is a germ cell tumor, pineal region tumor, medulloblastoma, or primary CNS lymphoma.

The pharmaceutical compositions described herein can be used to treat a disorder of the brain. In some embodiments, the brain disorder is a central nervous system disorder. In some embodiments, the central nervous system disorder is Parkinson's disease. In some embodiments, the central nervous system disorder is Parkinsonism, for example, cortigobasal degeneration (CBD), dementia with Lewy Bodies (DLB), drug-induced Parkinsonism, essential tremor, multiple system atrophy (MSA), progressive supranuclear palsy (PSP), or vascular (arteriosclerotic) parkinsonism. The pharmaceutical compositions described herein can be used to treat a brain injury. In some embodiments, the brain injury is mild traumatic brain injury (mTBI).

The present disclosure also describes the use of a compound or pharmaceutical composition to treat a CNS disorder. In some embodiments, the CNS disorder is addiction, an arachnoid cyst, attention deficit/hyperactivity disorder (ADHD), autism, bipolar disorder, catalepsy, depression, encephalitis, epilepsy, seizures, infection, locked-in syndrome, meningitis, migraines, multiple sclerosis, myelopathy, a neurodegenerative disorder, or Tourette's syndrome. In some embodiments, the CNS disorder is a neurodegenerative disorder. In some embodiments, the neurodegenerative disorder is Alzheimer's disease. In some embodiments, the neurodegenerative disorder is Huntington's disease. In some embodiments, the neurodegenerative disorder is Parkinson's disease.

Administering NAC, NAC amide, a NAC derivative, NAC congener, D-NAC, GSH, GSH derivative, or a pharmaceutically acceptable salt thereof can change the concentration of a NAC or GSH neurometabolite in a brain region. In some embodiments, the brain region is the cerebrum, brainstem, cerebellum, pons, medulla, frontal lobe, parietal lobe, occipital lobe, temporal lobe, left dorsal striatum, occipital cortex, substantia nigra, putamen, striatum, basal ganglia, or dorsolateral prefrontal cortex (DLPF). In some embodiments, the brain region is the occipital lobe. In some embodiments, the brain region is the occipital cortex. In some embodiments, the brain region is the cerebellum. In some embodiments, the brain region is the DLPF.

In some embodiments, the administering increases the concentration of a NAC or GSH neurometabolite in the brain region. In some embodiments, the administering increased the concentration of a NAC or GSH neurometabolite in the brain region by from about 20% to about 300%. In some embodiments, the administering increased the concentration of a NAC or GSH neurometabolite in the brain region by from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100%. In some embodiments, the administering increased the concentration of a NAC or GSH neurometabolite in the brain region by from about 100% to about 110%, from about 110% to about 120%, from about 120% to about 140%, from about 140% to about 160%, from about 160% to about 180%, from about 180% to about 200%, from about 200% to about 220%, from about 220% to about 240%, from about 240% to about 260%, from about 260% to about 280%, or from about 280% to about 300%.

In some embodiments, the administering increased the concentration of a NAC or GSH neurometabolite in the brain region by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%. In some embodiments, the administering increased the concentration of a NAC or GSH neurometabolite in the brain region by about 20%. In some embodiments, the administering increased the concentration of a NAC or GSH neurometabolite in the brain region by about 50%. In some embodiments, the administering increased the concentration of a NAC or GSH neurometabolite in the brain region by about 100%. In some embodiments, the administering increased the concentration of a NAC or GSH neurometabolite in the brain region by about 150%. In some embodiments, the administering increased the concentration of a NAC or GSH neurometabolite in the brain region by about 200%.

In some embodiments, the administering of NAC, NAC amide, a NAC derivative, NAC congener, D-NAC, GSH, GSH derivative, or a pharmaceutically acceptable salt thereof modulates the NAC or GSH neurometabolite/water ratio in a brain region. In some embodiments, the administering of NAC, NAC amide, a NAC derivative, NAC congener, D-NAC, GSH, GSH derivative, or a pharmaceutically acceptable salt thereof modulates the GSH/water ratio in a brain region. In some embodiments, the administering of NAC, NAC amide, a NAC derivative, NAC congener, D-NAC, GSH, GSH derivative, or a pharmaceutically acceptable salt thereof increases the GSH/water ratio in a brain region. In some embodiments, the administering of NAC, NAC amide, a NAC derivative, NAC congener, D-NAC, GSH, GSH derivative, or a pharmaceutically acceptable salt thereof modulates the NAA/water ratio in a brain region. In some embodiments, the administering of NAC, NAC amide, a NAC derivative, NAC congener, D-NAC, GSH, GSH derivative, or a pharmaceutically acceptable salt thereof increases the NAA/water ratio in a brain region.

In some embodiments, the administering of NAC, NAC amide, a NAC derivative, NAC congener, D-NAC, GSH, GSH derivative, or a pharmaceutically acceptable salt thereof increases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/water ratio in a region of the brain by about 10%. In some embodiments, the administering increases the GSH/water ratio in a region of the brain by about 20%. In some embodiments, the administering increases the GSH/water ratio in a region of the brain by about 30%. In some embodiments, the administering of NAC, NAC amide, a NAC derivative, NAC congener, D-NAC, GSH, GSH derivative, or a pharmaceutically acceptable salt thereof decreases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/water ratio in a region of the brain by about 10%. In some embodiments, the administering decreases the GSH/water ratio in a region of the brain by about 20%. In some embodiments, the administering decreases the GSH/water ratio in a region of the brain by about 30%.

In some embodiments, the administering of NAC, NAC amide, a NAC derivative, NAC congener, D-NAC, GSH, GSH derivative, or a pharmaceutically acceptable salt thereof increases the NAA/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/water ratio in a region of the brain by about 10%. In some embodiments, the administering increases the NAA/water ratio in a region of the brain by about 20%. In some embodiments, the administering increases the NAA/water ratio in a region of the brain by about 30%. In some embodiments, the administering of NAC, NAC amide, a NAC derivative, NAC congener, D-NAC, GSH, GSH derivative, or a pharmaceutically acceptable salt thereof increases NAA in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases NAA in a region of the brain by about 10%. In some embodiments, the administering increases NAA in a region of the brain by about 20%. In some embodiments, the administering increases NAA in a region of the brain by about 30%.

In some embodiments, the administering of NAC, NAC amide, a NAC derivative, NAC congener, D-NAC, GSH, GSH derivative, or a pharmaceutically acceptable salt thereof modulates the NAC or GSH neurometabolite/creatine ratio in a brain region. In some embodiments, the administering of NAC, NAC amide, a NAC derivative, NAC congener, D-NAC, GSH, GSH derivative, or a pharmaceutically acceptable salt thereof modulates the GSH/creatine ratio in a brain region. In some embodiments, the administering of NAC, NAC amide, a NAC derivative, NAC congener, D-NAC, GSH, GSH derivative, or a pharmaceutically acceptable salt thereof increases the GSH/creatine ratio in a brain region. In some embodiments, the administering of NAC, NAC amide, a NAC derivative, NAC congener, D-NAC, GSH, GSH derivative, or a pharmaceutically acceptable salt thereof modulates the NAA/creatine ratio in a brain region. In some embodiments, the administering of NAC, NAC amide, a NAC derivative, NAC congener, D-NAC, GSH, GSH derivative, or a pharmaceutically acceptable salt thereof increases the NAA/creatine ratio in a brain region.

In some embodiments, the administering of NAC, NAC amide, a NAC derivative, NAC congener, D-NAC, GSH, GSH derivative, or a pharmaceutically acceptable salt thereof increases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/creatine ratio in a region of the brain by about 10%. In some embodiments, the administering increases the GSH/creatine ratio in a region of the brain by about 20%. In some embodiments, the administering increases the GSH/creatine ratio in a region of the brain by about 30%. In some embodiments, the administering of NAC, NAC amide, a NAC derivative, NAC congener, D-NAC, GSH, GSH derivative, or a pharmaceutically acceptable salt thereof decreases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/creatine ratio in a region of the brain by about 10%. In some embodiments, the administering decreases the GSH/creatine ratio in a region of the brain by about 20%. In some embodiments, the administering decreases the GSH/creatine ratio in a region of the brain by about 30%.

In some embodiments, the administering of NAC, NAC amide, a NAC derivative, NAC congener, D-NAC, GSH, GSH derivative, or a pharmaceutically acceptable salt thereof increases the NAA/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/creatine ratio in a region of the brain by about 10%. In some embodiments, the administering increases the NAA/creatine ratio in a region of the brain by about 20%. In some embodiments, the administering increases the NAA/creatine ratio in a region of the brain by about 30%.

EXAMPLES

Example 1: Phase I Study of Brain Bioavailability and Safety of IN N2B NAC

A single site, single-blind, and open label six-part Phase 1 study in healthy volunteers is conducted to assess the brain bioavailability, safety, and tolerability of IN N2B NAC utilizing $^{1}$H-MRS measurement of NAC-derived neurometabolites. Brain bioavailability of NAC-derived neurometabolites is assessed for three doses of IN N2B NAC and compared to the effects of IN N2B GSH. Additionally, the effect of different formulations, dosing devices, and positioning during IN N2B administration are evaluated. Comparative brain bioavailability of NAC is measured following administration of NAC via IN, IV, or oral administration. The effects of 7-day repeat dosing of NAC via IN, IV, or oral administration are determined using $^{1}$H-MRS.

Measurements are obtained pre-dose and post-dose $^{1}$H-MRS of NAC-derived brain metabolites during single ascending and repeat dose studies of IN N2B NAC. Blood levels of NAC (free and total), cysteine, GSH and GSH/GSSG ratios are also obtained, and measurements of cerebrospinal fluid (CSF) NAC are obtained before and after 7 days of repeat dosing. Safety and tolerability are assessed through reports of adverse events, findings on physical neurologic examinations, laboratory test results, findings on the electrocardiogram (ECG), and specific assessment for nasal tolerability.

For each part of the study, participants undergo screening beginning up to 28 days prior to IP administration on Day 1. Subjects are required to sign an informed consent form (ICF) before undertaking any study-specific procedures or assessments. Participants who qualify for the study based on inclusion and exclusion criteria are enrolled. In each part of the study, safety is monitored by assessment of adverse events (AEs), vulnerability assessment scoring tool (VAS-T), and modified total nasal symptom (TNSS-M) scores, electrocardiogram (ECG) results, vital signs, physical and neurological examinations, blood tests and urine tests.

The pharmacokinetic (PK) and pharmacodynamic (PK) properties of a single dose of IN N2B GSH and single ascending doses of IN N2B NAC are determined by measuring the effect of the doses on NAC-derived neurometabolites as assessed by 1) $^{1}$H-MRS measurements of the N-cysteinyl resonances of GSH and NAC and the N-acetyl resonances of NAC and N-acetyl aspartate (NAA), expressed as ratios to the water or creatine resonance of voxels in the dorsolateral prefrontal cortex (DLPF), occipital lobe and striatum; and 2) peripheral blood concentrations of GSH, free and total NAC, cysteine and RBC GSH/GS SH ratios. In each part of the study, MRS analysis is completed and PK samples are drawn pre-dose and at 1, 3, 6 and 24 hours post-dose.

The effects of IN N2B NAC administered under different dosing conditions, formulations, using different devices, and participant positioning during IP administration are determined by measuring NAC-derived neurometabolites in the voxels of interest using MRS. The effects of twice-daily dosing of IN N2B NAC for 7 days on MRS-determined levels of 1) the aforementioned NAC-derived neurometabolites in the voxels of interest, 2) CSF NAC levels, and 3) peripheral blood concentrations of GSH, free and total NAC, cysteine and RBC GSH/GSSH ratios are measured.

Participant population: The study is conducted in 72 healthy male and female volunteers, inclusive at the time of informed consent. Women of childbearing potential (WOCBP) may be included and are subject to contraceptive requirements during the study from screening until study completion, including the follow-up period, and for at least 90 days after the last dose of IP. WOCBP must demonstrate negative pregnancy testing at screening and before administration of IP. The maximum duration of involvement for each participant, screening through study completion, is approximately 64-78 days.

Inclusion criteria: 1) Healthy volunteers between 18 and 45 years of age inclusive at the time of informed consent; 2) In good general health as determined by medical history, physical examination, vital signs, laboratory tests, and ECG. Isolated out-of-range values judged by the Principal Investigator (PI) or designated physician to be of no clinical significance can be allowed: the rationale for this determination must be recorded in the participant's source documents; 3) Have a body weight in the range of 50 to 120 kg, inclusive, and a body mass index (BMI) of 19 to 28 kg/m$^2$, inclusive, at screening; 4) Agree to abstain from alcohol intake for 24 hours prior to IP administration and 24 hours prior to all other outpatient clinic visits; 5) Agree not to use prescription medications (except for birth control) within 14 days prior to IP administration and for the duration of the study, unless approved by the PI and Sponsor Medical Monitor; 6) Agree not to use over the counter (OTC) medications (including corticosteroids, aspirin, pain medications, decongestants, antihistamines) and herbal medication (including St. John's Wort) within 14 days prior to IP administration through to the Day 7 follow-up visit, unless approved by the Medical Monitor. Occasional use of paracetamol (up to 2 g/day) is permitted; 7) Agree to refrain from participation in a competitive collision sport from the initiation of the screening period to the Day 28 follow up; 8) WOCBP must be non-pregnant and must use an acceptable, highly effective double barrier contraception from Screening until study completion, including the follow-up period. Double barrier contraception is defined as use of a condom (male or female, by self-declaration) AND one form of the following: established hormonal contraception (e.g., oral contraceptives pills [OCPs], long-acting implantable hormones, injectable hormones); a vaginal ring or an intrauterine device [IUD]); documented evidence of surgical sterilization at least 6 months prior to Screening (e.g., tubal occlusion, hysterectomy, bilateral salpingectomy, or bilateral oophorectomy); WOCBP who are in same-sex or not in any sexual relations (abstinence from heterosexual intercourse, by self-declaration) are not required to use contraception when this is their preferred and usual lifestyle. These WOCBP must agree to use the aforementioned acceptable, highly effective contraceptive method if beginning or planning to begin heterosexual relations from Screening until 90 days after the last dose of study drug. WOCBP must have a negative pregnancy test at Screening and Day −1 and be willing to have additional pregnancy tests as required throughout the study.

Women not of childbearing potential (non-WOCBP) must be postmenopausal for ≥12 months. Postmenopausal status is be confirmed through testing of follicle-stimulating hormone (FSH) levels ≥40 IU/mL at Screening for amenorrhoeic female participants. Non-WOCBP are not required to use contraception. Periodic abstinence (e.g., calendar, ovulation, symptothermal, post-ovulation-methods) and withdrawal are not considered highly effective methods of birth control. Male participants engaged in sexual relations with WOCBP must use an acceptable, highly effective double barrier contraceptive method from Screening until at least 90 days after the last dosing of study drug. Double barrier contraception is defined as use of a condom (male or female, by self-declaration) and, for WOCBP, use (by self-declaration) of an effective contraceptive including OCPs, long-acting implantable hormones, injectable hormones, a vaginal ring or an IUD (by self-declaration) or having received surgical sterilization (e.g., tubal occlusion, hysterectomy, bilateral salpingectomy, or bilateral oophorectomy).

Men in same-sex or not in any sexual relations (abstinence from heterosexual intercourse, by self-declaration) are not required to use contraception if this is their preferred and usual lifestyle. These men must agree to use the aforementioned acceptable, highly effective contraceptive method if beginning or planning to begin heterosexual relations with WOCBP from Screening until 90 days after the last dosing of study drug.

Exclusion criteria: 1) Females who are pregnant or nursing at Screening; 2) Have a deformity of the nasal cavity, a known deviation of the nasal septum; acute or chronic sinusitis or recent (<5 years) history of surgery of the nasal cavity and/or nasopharynx; 3) History of seizures or epilepsy within the past 5 years; 4) History of moderate to severe traumatic brain injury; 5) History of concussion within the past 1 year; 6) Currently have or have a history of any clinically significant medical illness or medical disorders the Investigator considers should exclude the participant, including (but not limited to) cardiovascular, neurologic, musculoskeletal, hematologic, respiratory, dermatologic, hepatic or neoplastic disease or immune deficiency state; 7) Psychiatric or behavioral condition which would compromise participation in the study; 8) Acute upper respiratory illness including a common cold, within 14 days prior to IP administration or have had a major illness or hospitalization within 1 month of Screening; 9) Major surgery within 12 weeks of Screening; 10) Any participant who plans to undergo elective surgery within 4 weeks prior to IP administration and through the end of the study including the follow-up period; 11) Positive serology test for HIV antibodies, hepatitis B surface antigen (HBsAg), or hepatitis C virus (HCV) antibodies at Screening; 12) Recent history (within previous 6 months) of alcohol or drug abuse; 13) Have smoked tobacco or related products within 3 months prior to dosing; 14) Have positive urine drug test at Screening and/or at any time during the study for substances of abuse including but not limited to cocaine, cannabinoids, amphetamines, benzodiazepines, opiates, tricyclic antidepressants, and methadone. Participants can be re-screened once following a positive result at the discretion of the Investigator; 15) Have a positive alcohol breath test at Screening and/or at any time during the study. Patients are required to abstain from alcohol for at least 24 hours prior to IP administration on Day 1 and on the day of study assessments; 16) Consume, on average, more than approximately 500 mg/day of caffeine (as contained in 5 cups of tea or coffee or 8 cans of soda or other caffeinated products) per day; 17) Donated blood within 60 days prior to Screening; 18) Have a history of active drug and/or food allergy or other active allergic disease requiring the constant use of medications, or a history of severe allergic reaction, angioedema or anaphylaxis; 19) Received any other experimental therapy including device or an investigational agent within 30 days or 5 half-lives (whichever is longer) of IP administration; 20) Are unable to undergo MRI scanning due to the presence of non-removable metal implants, including but not limited to surgical staples, pacemaker, steel IUD etc., claustrophobia or any other contraindication.

Statistical Methods

Pharmacokinetics: Changes in MRS spectra of the targeted metabolites and pharmacokinetic assessments (free and total NAC, cysteine and GSH concentrations and GSH/GSSG ratios and CSF NAC levels) from baseline to each post-dose timepoint are summarized using descriptive statistics.

Safety and tolerability: Participants provide a rating for IP tolerability several times during the study using a Visual Analog Scale (VAS), with a value of 0 indicating very good tolerability and 10 indicating very poor tolerability. The subjects also complete a TNSS-M, which assesses five specific nasal symptoms (i.e., congestion, runny nose, itching, pain and non-painful burning) on a 0 to 3 scale. Only items scored as a “3” (severe) on the TNSS-M are reported as adverse events.

Adverse events are coded using the most current version of the Medical Dictionary for Regulatory Activities (MedDRA®). A by-participant AE data listing, including verbatim term, preferred term (PT), system organ class (SOC), severity and relationship to IP, are provided. The number of participants experiencing treatment emergent adverse events (TEAEs), and the number of individual TEAEs are summarized by SOC, PT, and severity and relationship to IP. Laboratory evaluations, vital signs assessments, and ECG parameters are summarized for each scheduled visit. A summary of change from baseline at each protocol specified time point are presented.

Prior and concomitant medications are coded using the most current version of the World Health Organization (WHO) drug dictionary available at the start of the study and are listed by participant and summarized by treatment using anatomical therapeutic chemical (ATC) (level 2) and preferred name. Medical history, pregnancy/FSH testing, urine drug screen/alcohol breath test, physical and neurological examination, and serology (HIV, Hepatitis B and C screen) are listed by participant.

Primary objective: The primary objective of the study is to assess the brain bioavailability of IN N2B NAC using proton magnetic resonance spectroscopy ($^1$H-MRS) assessment of change from baseline in NAC-derived metabolic markers in healthy adult volunteers.

Secondary objectives: The secondary objectives of the study include: 1) Assessing the safety and tolerability of IN N2B NAC; 2) Assessing the time course and regional CNS pharmacodynamic activity of IN N2B NAC; 3) Comparing pharmacokinetic and pharmacodynamic activity of IN N2B NAC to IN N2B GSH; 4) Comparing devices and positioning during investigational product (IP) administration for optimal nose-to-brain delivery of IN N2B NAC; 5) Assessing the regional CNS pharmacodynamic activity and safety and tolerability of IN N2B NAC following multiple repeated IN dose; and 6) Assessing the pharmacokinetic profile of NAC in blood and cerebrospinal fluid (CSF) following IN administration.

Screen failures: Screen failures are defined as volunteers who consent to participate in the clinical study but are not subsequently enrolled. A minimal set of screen failure information is required to ensure transparent reporting of screen failure participants to meet the Consolidated Standards of Reporting Trials publishing requirements and to respond to queries from regulatory authorities. Minimal information includes screen failure details, eligibility criteria, and any serious adverse event (SAE). Individuals who do not meet the criteria for participation in this study (screen failure) are re-screened based on the judgement of the Investigator and in consultation with the medical monitor (MM). Re-screening is allowed within the recruitment period for the study. Re-screened participants are assigned the same participant number as for the initial Screening.

Participant replacement: Participants who sign the informed consent form (ICF) and are enrolled but do not receive IP may be replaced. Participants who sign the ICF, are enrolled and receive IP but subsequently withdraw, or are withdrawn or discontinued from the study, are replaced at the discretion of the Sponsor.

Participant withdrawal criteria: Participants can withdraw consent to participate in the study at any time. If a participant withdraws consent, the date and reason for consent withdrawal are documented. Participants are encouraged to remain in the clinic to complete all necessary assessments and until the Investigator deems that discharge is safe. Participant data are included in the analysis up to the date of the withdrawal of consent.

The primary reason for withdrawal is identified and recorded on the appropriate eCRF, along with the date of withdrawal. In accordance with applicable regulations, a participant has the right to withdraw from the study, at any time and for any reason, without prejudice to future medical care. If a participant is withdrawn because of an AE, the Investigator arranges for the participant to have appropriate follow-up care until the AE is resolved or has stabilized. Unresolved AEs are followed until the last scheduled Follow-up visit or until the PI and MM determine that further follow-up is no longer indicated. In addition to AEs, other reasons for removal of participants from the study can include, but are not limited to, withdrawal of consent, administrative decision by the Investigator or the Sponsor, protocol deviation, or participant noncompliance.

If a participant asks or decides to withdraw from the study, all efforts are made to complete and report the observations, especially the listed primary and secondary objectives, as thoroughly as possible up to the date of withdrawal. Wherever possible, the tests and evaluations, including those listed for the Follow-up Visit, are performed for all participants who discontinue prior to the completion of the study.

Participant termination criteria: Reasons for early termination of individual participants can include: Protocol deviations or participant non-compliance (must be specified on the appropriate electronic case report form [eCRF]); Pregnancy; Serious or severe AEs; Administrative decision by the Investigator or the Sponsor; Death; or Other (must be specified).

Lost to follow-up: A participant is considered lost to follow-up if the participant fails to return for one of the scheduled visits and is unable to be contacted by the study staff. The following actions are taken if a participant fails to return for a required study visit: The site attempts to contact the participant and reschedule the missed visit within 2 days and counsel the participant on the importance of maintaining the assigned visit schedule and ascertain if the participant wishes to continue in the study; Before a participant is deemed lost to follow-up, the Investigator or designee makes every effort to regain contact with the participant (three telephone calls and contact via email and text message). These contact attempts are documented in the participant's medical record or study file. The participant is considered to have withdrawn from the study with a primary reason of lost to follow-up if the staff cannot contact the participant.

Example 2: NAC Sol-Gel Formulation

Participants receive one or more of IP formulation and dosage of NAC. A dose of IN N2B NAC yielding an increase in brain GSH of approximately 13% is considered the minimal effective dose.

A 16.6% solubilized gelling (sol-gel) solution comprises a solution containing a thermoresponsive, polymeric gelling agent and is administered in liquid form. The solution undergoes in situ gelation, resulting mucoadhesion and sustained drug delivery. The gel formulation is administered at one of the following doses: i) 100 mg (0.6 mL)—approximately 0.3 mL in each nostril per dose; ii) 200 mg (1.0 mL)—approximately 0.6 mL in each nostril per dose; or iii) 400 mg (2.0 mL)—approximately 0.6 mL once in each nostril, with repeat administration after 5 minutes. The sol-gel solution is administered intranasally using an Aptar CPS Nasal Pump.

TABLE 1 lists details of the NAC sol-gel formulation. TABLE 2 lists the gelation characteristics of the NAC sol-gel formulation.

TABLE 1

| Component | % w/w | Role |
|---|---|---|
| NAC | 16.6 (w/v) | Active ingredient |
| Poloxamer 407 | 13.0 | Thermoresponsive polymer, mucoadhesive |
| Poloxamer 188 | 2.8 | Viscosity and gelation temperature modifier |
| Hydroxypropyl methylcellulose E4M | 0.1 | Mucoadhesive agent |
| Methyl paraben | 0.1 | Preservative |

TABLE 2

| Characteristic | Value |
|---|---|
| Gelation temp (° C.) | 27.34 (±1.24) |
| Gel Strength (Pa) at 8° C. | 0.03 (±0.001) |
| Gel Strength (Pa) at 34° C. | 7399.33 (±61.84) |
| Viscosity (Pa · s) at 8° C. | 0.176 (±0.01) |
| Viscosity (Pa · s) at 34° C. | 2.17 (±0.04) |

Example 3: Study Evaluations and Measurements

Pharmacodynamic assessments: Pharmacodynamic assessments include change from baseline in NAC-derived neurometabolite concentrations in three brain regions (i.e., occipital cortex, striatum, and DLPF), using $^{1}$H-MRS following a single dose of IN N2B NAC in healthy volunteers at 1, 3, 6 and 24 hours post-dose.

$^{1}$H-MRS analysis is performed using 3.0 cm×3.0 cm×2.5 cm voxels placed in the left dorsal striatum at the level of the lentiform nucleus, the occipital cortex, and the dorsolateral prefrontal cortex (DLPF). A J-edited spin echo difference method is implemented with an echo time (TE) of 70 ms and a repetition time (TR) of 1500 ms using 240 interleaved excitations (480 total) for an acquisition time of 12.5 minutes per voxel. A pair of frequency-selective inversion pulses are inserted into the standard point-resolved spectroscopy method and applied on alternate scans at the frequency of the reduced form of glutathione α-cysteinyl resonance at 4.56 ppm while avoiding excitation of the oxidized form of glutathione α-cysteinyl resonance at 3.28 ppm. Subtracting the two, resulting inverted subspectra of GSH yield a $^{1}$H-MRS only consisting of GSH β-cysteinyl resonance at 2.98 ppm. The 32-channel phased-array coil GSH data are combined into a single regular time-domain free-induction decay signal using the unsuppressed voxel tissue water signal from each receiver coil element to derive the required relative phased-array coil sensitivities. The metabolite concentrations are estimated by calculating the areas of the individual spectral peaks obtained by frequency-domain fitting each resonance to a Gauss-Lorentz lineshape function using the Levenberg-Marquardt non-linear least-squares algorithm.

Pharmacokinetic assessments: Pharmacokinetic assessments include peripheral blood measurements of GSH, cysteine, free and total NAC and reduced-to-oxidized GSH ratio (GSH/GSSG) ratios at 1, 3, 6, and 24 hours following IN NAC or GSH administration, and levels of CSF NAC obtained via lumbar puncture 6 hours following IP administration in Parts 5 and 6 of the study.

Blood PK sample collection: Blood PK samples are collected as close as possible prior to the acquisition of MRS data at each time point specified in the Schedule of Assessments. Blood PK measures free and total NAC, cysteine and GSH concentrations and GSH/GSSG ratio. GSH/GSSG is measured in whole blood using high performance liquid chromatography (HPLC) coupled to a mass spectrometer (MS). Total protein-bound and total protein-unbound concentrations of NAC, Cys and GSH are measured in plasma using a validated HPLC-MS assay.

Pharmacodynamic endpoints: MRS of NAC-derived brain metabolites in three regions of interest (occipital cortex, striatum, DLPF) at baseline and at 1, 3 and 6 hours following IN N2B NAC are summarized using descriptive statistics. Change from baseline to each post-dose measurement are summarized descriptively. No a priori inferential statistical tests are planned. Brain regions of interest and timing of MRS are modified based on initial results.

Pharmacokinetic endpoints: A descriptive summary of the quantifiable concentrations of the targeted metabolites are reported for the specified time points to assess free and total NAC, cysteine and GSH concentrations and reduced-to-oxidized GSH ratio (GSH/GSSG).

Safety and tolerability: All safety assessments, including prior and concomitant medications, AEs, laboratory evaluations, vital signs, ECGs, and other safety assessments are summarized using the Safety Population.

Prior and concomitant medication: Prior and concomitant medications are coded using the most current version of the WHO drug dictionary available at the start of the study. Prior and concomitant medications are listed by participant and summarized by treatment using ATC (level 2) and preferred name.

Adverse events: Adverse events re coded using the most current version of the MedDR® available. A by participant AE data listing, including verbatim term, PT, SOC, severity and relationship to IP, are provided. The number of participants experiencing TEAEs, and the number of individual TEAEs are summarized by SOC, PT, severity and relationship to IP.

Other safety assessments: Other safety assessments listed by participant include: medical history, pregnancy test, urine drug screen, alcohol breath test, physical and neurological examination, and serology (e.g., HIV, Hepatitis B, Hepatitis C).

Safety parameters: Study procedures are completed as delineated in the Schedule of Assessments. If a participant is unable to attend a visit within the specified window, the Investigator or designee discusses appropriate scheduling with the Sponsor's MM or appropriate designee. Any unscheduled procedures required for urgent evaluation of safety concerns take precedence over all routine scheduled procedures.

Demographic and medical history: Medical history (e.g., concomitant mediations, alcohol and smoking status, and drug use), date of birth, age (calculated), sex, ethnicity, and race are recorded at Screening.

Vital signs: Vital signs (e.g., blood pressure [systolic and diastolic], pulse rate, respiratory rate, and body temperature) are listed and summarized at protocol specified collection time point. Observed and change from baseline are summarized at each protocol specified collection time point. When the time of vital signs measurement coincides with a blood draw, the vital signs are taken before the scheduled blood draw where possible, ensuring the blood draw is within the window specified in the protocol. Additional vital signs are performed at other times if deemed necessary.

Weight and height: Body height and body weight are measured at Screening and are used to calculate BMI. BMI is calculated by dividing the participant's body weight in kilograms by the participant's height in meters squared (kg/m2). Body weight and height are obtained with the participant's shoes and jacket or coat removed.

Physical and neurological examination: Full and brief physical and neurological examinations are performed by a licensed physician at the time points specified in the Schedule of Assessments. Full physical examinations include: general appearance, head, ears, eyes, nose, throat, dentition, thyroid, chest (heart, lungs), abdomen, skin, neurological, extremities, back, neck, musculoskeletal, and lymph nodes. The neurological examination includes assessment of mental status and function of cranial nerves, motor and sensory systems, gait/coordination and deep tendon reflexes. Brief physical examination includes: head, ears, eyes, nose, throat, chest (heart, lungs), abdomen, skin, musculoskeletal, and lymph nodes and any pertinent system based on any prior findings. Brief neurologic examination includes assessment of eye movements, facial symmetry, drift of upper extremities, coordination (finger-to-nose and heel-toe testing) and deep tendon reflexes. Physical and neurological examinations are performed at various unscheduled time points if deemed necessary by the Investigator.

Tolerability assessments: Participants provide a rating for IP tolerability at specified times during the study using VAS-T with a value of 0 indicating very good tolerability and 10 indicating very poor tolerability. Participants also complete TNSS-M, which assesses five specific nasal symptoms (congestion, runny nose, itching, pain and non-painful burning) on a 0 to 3 scale. Only items scored as a "3" (severe) on the TNSS-M are reported as adverse events.

Electrocardiograms: ECG values are listed and summarized at protocol specified collection time point. Observed and change from baseline are summarized at each protocol specified collection time point. A 12-lead ECG are taken at the time points delineated in the Schedule of Assessments. Additional ECG monitoring are performed at other times if deemed necessary. ECGs are performed prior to vital signs with participants in a supine position. Participants are in supine position for at least 5 minutes before the reading is taken. All ECG tracings are reviewed by the PI or designee. When the time of ECG monitoring coincides with a blood draw, the ECG is taken before the scheduled blood draw while ensuring the blood draw is within the window specified in the protocol.

Laboratory evaluations: Laboratory evaluations, including hematology, serum chemistry and urinalysis, are listed and summarized at each protocol specified collection time point. Observed and change from baseline clinical laboratory data are summarized at each protocol specified collection time point. A blood sample for safety laboratory testing (hematology, serum chemistry, and urinalysis) are taken at the time points specified in the Schedule of Assessments. Additional clinical laboratory tests are performed at other times if deemed necessary based on the participant's clinical condition.

Hematology parameters tested are: hemoglobin (HGB); hematocrit (HCT); erythrocytes (RBC); platelets (PLAT); leukocytes with differential, including Eosinophils (ESN), Neutrophils (NEUT), Basophils (BASO), Lymphocytes (LYM), and Monocytes (MONO). Serum chemistry parameters tested are: urea (BUN); creatinine (CREAT); total Bilirubin (BILI) and Direct Bilirubin (BILIDIR); urate (URATE); albumin (ALB); globulin (GLOBUL); alkaline Phosphatase (ALP); creatine Kinase (CK); aspartate Aminotransferase (AST); alanine Aminotransferase (ALT); gamma-GT (GGT); glucose (GLU); sodium (NA); potassium (K); calcium (CA); chloride (CL); phosphate (PHOS); bicarbonate (BICARB); and lactate dehydrogenase (LDH).

Urinalysis: A urinalysis test (dipstick) is performed for each participant. Urinary analysis is performed at Screening. If abnormality is noted for protein, blood, nitrite or leukocyte esterase (and at the discretion of the Investigator), a microscopic examination of red blood cells, white blood cells, bacteria and casts are performed. Macroscopic urinalysis parameters to be tested are: pH (PH); specific gravity (SPGRAV); creatinine (CREATININE); protein (PROT); glucose (GLUC); ketones (KETONES); total Bilirubin (BILI); occult Blood (OCCBLD); nitrite (NITRITE); urobilinogen (UROBIL); and leukocytes (WBC).

Viral serology: HBsAg, anti-HCV and HIV antibody testing are performed at Screening.

Urine drug screen and alcohol breath test: A urine drug screen is performed at Screening, prior to dosing on Day 1, and at the Day 7 Follow-up Visit. The urine drug screen includes but is not limited to cocaine, cannabinoids, amphetamines, benzodiazepines, opiates, tricyclic antidepressants and methadone. An alcohol breath test is performed at Screening, prior to dosing on Day 1, and at the Day 7 Follow-up Visit.

Pregnancy testing and follicle-stimulating hormone testing: A serum pregnancy test is performed at the Screening visit for WOCBP only. A urine pregnancy test is performed prior to dosing on Day 1. If the result is positive, a serum test is performed for confirmation. Women not of childbearing potential must be postmenopausal (defined as cessation of regular menstrual periods for at least 12 months). Postmenopausal status is confirmed through testing of FSH levels ≥40 IU/mL at Screening.

Adverse and serious adverse events: AEs are reported for all participants from the time of consent until the completion of the Follow-up Visit. Serious adverse events are reported for all participants (enrolled and not enrolled) from the time of consent until the completion of the Follow-up Visit. Adverse events reported from the time of consent up until dosing are recorded as pre-treatment AEs. Treatment-emergent AEs (TEAEs) are evaluated from the first administration of IP until the Follow-up Visit or up to a 30-day follow-up period for AEs deemed related to treatment. Adverse events that are ongoing at the final follow-up are marked as Not Recovered/Not resolved on the AE eCRF page. All spontaneously volunteered and enquired for, as well as observed AEs, are recorded in the participant's medical records and the eCRF.

An AE is any event, side-effect, or other untoward medical occurrence that occurs in conjunction with the use of a medicinal product in humans, whether or not considered to have a causal relationship to this treatment. An AE can be any unfavorable and unintended sign that can include a clinically significant abnormal laboratory finding, symptom, or disease temporally associated with the use of a medicinal product, whether or not considered related to the medicinal product.

Events meeting the definition of an AE include: 1) exacerbation of a chronic or intermittent pre-existing condition including either an increase in frequency and/or intensity of the condition; 2) new conditions detected or diagnosed after IP administration that occur during the reporting periods, even though the condition may have been present prior to the start of the study; 3) signs, symptoms, or the clinical sequelae of a suspected interaction; and 4) signs, symptoms, or the clinical sequelae of a suspected overdose of either IP or concomitant medications (overdose per se is be reported as an AE/SAE)

Events that do not meet the definition of an AE include: 1) Medical or surgical procedure (e.g., endoscopy, appendectomy); the condition that leads to the procedure is reported as an AE if the condition meets the criteria of an AE; 2) situations where an untoward medical occurrence did not occur (e.g., social and/or convenience admission to a hospital); and 3) anticipated day-to-day fluctuations of pre-existing disease(s) or condition(s) present or detected at the start of the study that do not worsen. If there is evidence of an AE through report or observation, the Investigator or designee evaluates further and record the following information: time of onset and resolution; severity; seriousness; causality/relation to study treatment; action taken regarding IP; action taken regarding AE; and outcome. Only items scored as a "3" (severe) on the TNSS-M are reported as adverse events.

Severity of an adverse event: Severity of AEs is graded by the Investigator as one of: 1) Mild (Grade 1): A type of AE that is usually transient and may require only minimal treatment or therapeutic intervention. The event does not generally interfere with usual activities of daily living; 2) Moderate (Grade 2): A type of AE that is usually alleviated with additional specific therapeutic intervention. The event interferes with usual activities of daily living, causing discomfort but poses no significant or permanent risk of harm to the research participant; 3) Severe (Grade 3): A type of AE that interrupts usual activities of daily living, or significantly affects clinical status, or may require intensive therapeutic intervention; 4) Life-threatening (Grade 4): A type of AE that places the participant at immediate risk of death; and 5) Death (Grade 5): Events that result in death.

Causal relationship of an adverse event: The Investigator assesses the relationship between IP and the occurrence of each AE. The Investigator's assessment of the relationship of each AE to IP is recorded in the source documents and the eCRF. Alternative causes, such as medical history, concomitant therapy, other risk factors, and the temporal relationship of the event to the IP is considered and investigated, if appropriate. The following definitions are general guidelines to help assign grade of attribution: 1) Not related: The event is clearly related to other factors such as the participant's environment or clinical state, therapeutic interventions or concomitant drugs administered to the participant. This is especially so when an event occurs prior to the commencement of treatment with the IP; 2) Unlikely: The temporal association, participant history, and/or circumstances are such that the IP is not likely to have had an association with the observed event. Other conditions, including concurrent illness, progression, or expression of the disease state, or reaction to a concomitant drug administered appear to explain the event; 3) Possible: The event follows a reasonable temporal sequence from the time of IP administration or follows a known response to the IP but could have been produced by other factors such as the participant's clinical state, other therapeutic interventions, or concomitant drugs administered to the participant; 4) Probable: The event follows a reasonable temporal sequence from the time of IP administration and follows a known response to the IP and cannot be reasonably explained by other factors such as the participant's clinical state, other therapeutic interventions, or concomitant drugs administered to the participant; and 5) Definite: The event follows a reasonable temporal sequence from the time of IP administration or control abates upon discontinuation or cannot be explained by known characteristics of the participant's clinical state.

Expectedness: The MM is responsible for determining whether an AE is expected or unexpected. An AE is considered unexpected if the nature, severity, or frequency of the event is not consistent with risk information.

Outcome: Outcome of an AE is recorded on the AE eCRF as follows: recovered/resolved; recovering/resolving; recovered/resolved with sequelae; not recovered/not resolving; fatal; and unknown.

Definition of serious adverse event: An SAE is an AE occurring during any study phase (i.e. baseline, treatment, or follow-up), and at any dose of the IP, that fulfils one or more of the following: results in death; immediately life-threatening; requires in-patient hospitalization or prolongation of existing hospitalization; results in persistent or significant disability or incapacity; results in a congenital abnormality or birth defect; is an important medical event that jeopardize the participant or requires medical intervention to prevent one of the outcomes listed above. An AE is considered life-threatening if, in the opinion of either the Investigator or the Sponsor, the occurrence places the participant at immediate risk of death.

Notification of a serious adverse event: All SAEs are reported within 24 hours from the time the site investigational team becomes aware of the event to meet requirements for expedited reporting of SAEs to applicable regulatory authorities and institutional ethics committees. Initial reporting is achieved by completing an SAE report form and email the assigned project email address, which is provided upon study setup. If completion of an SAE form and emailing is not possible, reporting by telephone is required and a completed SAE form must be emailed at the first opportunity. Initial notification of an SAE by telephone is confirmed in writing 24 hours from the time the site investigational team first becomes aware of the event using the SAE report form as described above. As further information regarding the SAE becomes available, such follow-up information is documented on a new SAE report form, marked as a follow-up report, scanned and emailed to the address at the bottom of the report form.

Withdrawal from the study in the event of an SAE and therapeutic measures taken are at the discretion of the Investigator. A full explanation for the discontinuation from the study are made in the participant's medical records and in the CRF. The Sponsor or their designee is responsible for notifying the relevant regulatory authorities of certain events. The Investigator is also be notified of all unexpected, serious, drug-related events that occur during the clinical trial. The investigational site is responsible for notifying its IRB/EC of these additional SAEs, if required.

Clinical Laboratory Abnormalities and Other Abnormal Assessments as Adverse Events and Serious Adverse Events: Abnormal laboratory findings (e.g. serum chemistry and hematology) or other abnormal assessments (e.g. ECG and vital signs) per se are not reported as AEs. However, those abnormal findings that are deemed clinically significant by the PI and/or delegate or are associated with signs and/or symptoms are recorded as AEs if the findings meet the definition of an AE (and recorded as an SAE if the findings meet the criteria of being serious) as previously described. Clinically significant abnormal laboratory or other abnormal findings that are detected after consent or that are present at baseline and worsen after consent are included as AEs (and SAEs if serious). The Investigator exercises medical and scientific judgement in deciding whether an abnormal laboratory finding, or other abnormal assessment is clinically significant. To be considered clinically significant, the abnormality is associated with a clinically evident sign or symptom or be likely to result in an evident sign or symptom in the near term. A clinically significant laboratory abnormality in the absence of clinical symptoms can jeopardize the participant and can require intervention to prevent immediate consequences. For example, a markedly low serum glucose concentration can not be accompanied by coma or convulsions yet be of a magnitude to require glucose administration to prevent such sequelae.

Recording adverse events: Adverse events spontaneously reported by the participant and/or in response to an open question from the study personnel or revealed by observation are recorded in accordance with the Investigator's normal clinical practice and on the AE page of the eCRF during the study at the investigational site. Abnormal values that constitute an SAE or lead to discontinuation of administration of IP must be reported and recorded as an AE. Information about AEs and SAEs are collected from the time of consent until the end of the study. The AE term are reported in standard medical terminology when possible. For each AE, the Investigator evaluates and reports the onset (date and time), resolution (date and time), intensity, causality, action taken, serious outcome (if applicable), and whether or not the AE caused the participant to discontinue the study. AEs that occur during the study are documented in the participant's medical record, on the AE eCRF and on the SAE report form. If an SAE report is completed, pertinent laboratory data is recorded on the SAE form, preferably with baseline values and copies of laboratory reports.

If the abnormal assessment meets the criteria for being serious, the SAE form is also to be completed. A diagnosis, if known, or clinical signs or symptoms if the diagnosis is unknown, is used to complete the AE/SAE page. If no diagnosis is known and clinical signs or symptoms are not present, then abnormal finding is recorded.

Follow-up of Adverse Events and Serious Adverse Events: All AEs and SAEs that are deemed related, possibly related or probably related to the IP are followed until resolution, until the condition stabilizes, until the event is otherwise explained, or until the participant dies or is lost to follow-up. The Investigator is responsible for ensuring that follow-up includes any supplemental investigations as may be indicated to elucidate as completely as practical the nature and/or causality of the AE/SAE. Additional laboratory tests or investigations or consultation with other health care professionals are included. The Sponsor can request that the Investigator perform or arrange for the conduct of supplemental measurements and/or evaluations. If a participant dies during participation in the study or during a recognized follow-up period, the Sponsor is provided with a copy of any post-mortem findings, including histopathology.

Pregnancy: Pregnancy testing is performed in all WOCBP at Screening and Day 1 as per the Schedule of Assessments, and the pregnancy results is captured in the eCRF. All WOCBP re instructed to contact the Investigator immediately if pregnancy is likely (e.g., missed or late menstrual period) at any time during the trial. Male participants contact the Investigator immediately upon suspicion of fathering a child during the study treatment period. When possible, the partner's pregnancy is followed (to term) to determine the outcome. Should a pregnancy occur, the pregnancy must be reported and recorded on a Pregnancy Form. Pregnancy is not regarded as an AE unless a suspicion exists that the IP have interfered with the effectiveness of a contraceptive medication. The Investigator reports the details on a Pregnancy Form to the Sponsor/assigned designee within 24 hours of knowledge of the pregnancy. Even though participants agree to withdraw or terminate the clinical trial, the Investigator follows-up and documents the process and results of all the pregnancies.

If a male participant's female partner becomes pregnant while enrolled in the trial, a Pregnancy Form is completed and sent to the Clinical Research Organization (CRO) expeditiously, irrespective of whether the pregnancy meets the criteria for expedited reporting. Abortions (spontaneous, accidental, or therapeutic) are also reported. Congenital anomalies/birth defects always meet SAE criteria, and is therefore be expeditiously reported as an SAE, using the previously described process for SAE reporting. A Pregnancy Form is updated to reflect the outcome of the pregnancy. The Investigator reports any pregnancy (including pregnancy of a male participant's partner), even if no AE has occurred, on a Pregnancy Report Form within 24 hours of the Investigator becoming aware of the pregnancy

Example 4: Formulation Comparison Study

Ten study participants are randomized in a 1:1 ratio to two dosing cohorts. One cohort receives acetylcysteine 20% solution on Day 1, followed 7 days later by a NAC sol-gel solution, with the other cohort assigned to the reverse sequence of formulation dosing. The dose of IN N2B NAC—100, 200 or 400 mg—and the device utilized for IP administration is selected based the results of the single ascending dose study and the dose comparison study.

MRS is performed, and blood samples are collected to determine peripheral blood concentrations of GSH, cysteine, free and total NAC and RBG GSH/GSSG ratios prior to IP administration. MRS is repeated 1, 3, 6, and 24 hours post-dose. Changes from baseline in the relative levels of NAC-derived neurometabolites are assessed following administration of single doses of IN N2B NAC as a NAC 20% solution or a NAC sol-gel solution. The NAC sol-gel solution is a 16.6% solubilized gelling (sol-gel) solution comprising a thermoresponsive, polymeric gelling agent that is administered in liquid form and that undergoes in situ gelation, with resulting mucoadhesion and sustained drug delivery. TABLE 3 shows the dose cohorts for the formulation comparison study.

TABLE 3

| Cohort | Day 1 | Day 8 |
|---|---|---|
| 3A | Acetylcysteine 20% solution | NAC sol-gel |
| 3B | NAC sol-gel | Acetylcysteine 20% solution |

The 20% NAC and NAC sol-gel solutions are administered intranasally with the participant in a supine or seated position as instructed. During the study, a participant receives 0.5 mL, 1 mL, or 2 mL of the 20% NAC solution; 1 mL of a 20% GSH solution; or 0.6 mL, 1.2 mL, or 2.4 mL of the 16% NAC sol-gel solution. For all doses, approximately half of the total dose is administered into each nostril.

Using the Teleflex MAD device, NAC doses are administrated as follows: 1) IN N2B NAC 100 mg (0.5 mL): 0.25 mL per spray, one spray in each nostril; 2) IN N2B NAC 200 mg (1 mL) or IN N2B GSH 200 mg (1 mL): 0.25 mL per spray, two sprays in each nostril; or 3) IN N2B NAC 400 mg (2 mL): 0.5 mL per spray, two sprays in each nostril, with repeat administration of two sprays in each nostril after 5 minutes. Using the Aptar CPS Nasal Pump, NAC doses are administered as follows: 1) IN N2B NAC 100 mg (0.5 mL): 0.14 mL per spray, 2 sprays in each nostril; 2) IN N2B NAC 200 mg (1 mL) or IN N2B GSH 200 mg (1 mL): 0.14 mL per spray, 4 sprays in each nostril; 3) IN N2B NAC 400 mg (2 mL): 0.14 mL per spray, 4 sprays in each nostril, with repeat administration after 5 minutes of 4 sprays in each nostril; 4) NAC sol-gel solution with 100 mg NAC (0.6 mL): 0.14 mL per spray, up to 2 sprays in each nostril; 5) NAC sol-gel solution with 200 mg NAC (1.2 mL): 0.14 mL per spray, up to 4 sprays in each nostril; 6) NAC sol-gel solution with 400 mg NAC (2.4 mL): 0.14 mL per spray, up to 4 sprays in each nostril, with repeat administration of 4 sprays in each nostril after 5 minutes.

Participants self-administer IN N2B NAC up to 400 mg one to three times daily using the Aptar CPS Nasal Pump. On assessment days, IN N2B NAC is administered by site staff. Participants are trained by site staff on the use of the Aptar CPS Nasal pump.

When the formulation for administration is the NAC sol-gel solution, participants irrigate the sinuses using isotonic saline solution with an irrigation bottle following the conclusion of the 6-hour post-dose MRS scan. If the participant is experiencing congestion or other discomfort, nasal irrigation can be performed at any time, preferably not until the 1-hour post-dose MRS is completed. Additionally, the participant is discouraged from blowing the nose until completion of the 6-hour post-dose MRS. Safety and tolerability are monitored as outlined in TABLE 5. Participants experiencing treatment-limiting adverse effects are discontinued from the study. Participants return for a Follow-up Visit 7 days following the last dose of IP (Day 36±3 days) and receive a follow-up telephone call on Day 57 (±2 days) for safety assessment.

The effects of oral administration of NAC are also compared to IN N2B NAC. 200 mg/mL of acetylcysteine as a 20% w/v solution is used. NAC is orally administered by diluting the NAC solution in a diet soft drink to a concentration of 5%. The oral dose studied is a 4,000 mg dose, which is prepared by adding 20 mL of a 20% NAC solution in 60 mL of diet soda to yield 80 mL of a 5% NAC solution.

The effects of IV NAC is also compared to IN N2B NAC. Acetadote 200 mg/mL injection or an equivalent is administered by site staff. Acetadote is hyperosmolar (2000 mOsm/L), so Acetadote is diluted prior to injection. Acetadote is diluted in a 0.45% saline solution (½ normal saline). The dosage of IV NAC administered is 150 mg/kg, which is diluted in 200 mL of 0.45% saline solution and infused over 1 hour. TABLE 4 lists example dosages by weight of 200 mg/mL IV NAC.

TABLE 4

| Body weight (kg) | Dose of Acetadote (acetylcysteine 200 mg/mL) solution for injection 150 mg/kg in 200 mL of 0.45% saline solution infused over 1 hour, mg |
|---|---|
| 50 | 7,500 |
| 60 | 9,000 |
| 70 | 10,500 |
| 80 | 12,000 |
| 90 | 13,500 |
| ≥100 | 15,000 |

TABLE 5

| | Activity | | | | | | | |
|---|---|---|---|---|---|---|---|---|
| | Screening visit[1] | Dosing Day 1 | Dosing Day 2 | Dosing Days 3-6 | Dosing Day 7 | Post-Dose | Study Follow-up Visit | Telephone call |
| | Day −28 to −1 | Day 1 | Day 2 | Days 3 to 6 | Day 7 | Day 8 | Day 14 | Day 35 |
| Screening/Administrative/Other Assessments | | | | | | | | |
| Informed consent | X | | | | | | | |
| Demography | X | | | | | | | |
| Eligibility criteria | X | X | | | | | | |
| Medical and medication history | X | | | | | | | |
| Drug/alcohol screen | X | X | | | | | | |
| Laboratory tests[2] | X | | | | | | | |
| Enrollment | | X | | | | | | |

TABLE 5-continued

| | Activity | | | | | | | |
|---|---|---|---|---|---|---|---|---|
| | Screening visit[1] Day −28 to −1 | Dosing Day 1 Day 1 | Dosing Day 2 Day 2 | Dosing Days 3-6 Days 3 to 6 | Dosing Day 7 Day 7 | Post-Dose Day 8 | Study Follow-up Visit Day 14 | Telephone call Day 35 |
| Safety Assessments | | | | | | | | |
| Physical exam | X | | | | | | X | |
| Brief physical exam | | X | X | X | X | X | | |
| Neurologic exam | X | | | | | | X | |
| Brief neurologic exam | | X | X | X | X | X | | |
| Vital signs | X | | X | X | X | X | X | |
| Height | X | | | | | | | |
| Weight | X | | | | | | X | |
| 12-lead ECG[3] | X | X | | | | | X | |
| Laboratory tests[2] | | X | | | | | X | |
| Urinalysis | X | | | | | | X | |
| VAS-tolerability | | X | X | X | X | | | |
| TNSS-M | X | X | X | X | X | X | X | X |
| Adverse event monitoring | X | X | X | X | X | X | X | X |
| Concomitant meds | X | X | | | | X | X | X |
| IP Administration/MRS/Pharmacokinetic Assessments | | | | | | | | |
| IP dosing[4] | | X | X | X | X | | | |
| MRS[5] | | X | X | | X | X | | |
| CSF NAC & GSH[6] | | X | | | X | | | |
| Plasma GSH, cysteine, free and total NAC[7] | | X | X | | X | X | | |
| RBC GSH/GSSG[7] | | X | X | | X | X | | |

ABBREVIATIONS:
ECG, electrocardiogram;
GSH, glutathione
GSH/GSSG, reduced-to-oxidized glutathione;
MRS, magnetic resonance spectroscopy;
NAC, N-acetylcysteine;
TNSS-M, Modified Total Nasal Symptom Scale;
VAS-T, Visual Analog Scale for Tolerability
[1]Screening procedures must occur within 28 days of Day 1 IP dosing
[2]See Laboratory assessments for list of tests to be completed.
[3]ECG should be performed pre-dose on Days 1 and 7
[4]BID or TID dosing depending on Parts 1&2.
[5]MRS pre-dose and 1, 3, 6 and 24 hours post-day 1 morning dose and post-day 7 morning dose
[6]CSF sampling on Days 1 and Day 7 following the 6-hour post-dose MRS
[7]Blood samples for NAC, cysteine, GSH and RBC GSH/GSSG drawn prior to each MRS session.

All medications, including over-the-counter medications, vitamins, and herbal supplements, taken during the 30 days prior to the first NAC administration are recorded and reviewed by the Investigator to determine whether the participant is suitable for inclusion in the study. Prior therapy or concomitant therapy with any medications, including both prescription and non-prescription drugs are discussed with the Investigator and Sponsor's MM before IP administration, except in the case of necessary treatment of AEs or where appropriate medical care necessitates that therapy should begin before the Investigator can consult with the MM. The use of any NAC or investigational medical device within 30 days prior to Screening is prohibited. Paracetamol/acetaminophen (1-2 therapeutic doses per week) can be used for minor ailments during the course of the study, at the discretion of the Investigator, without prior consultation with Sponsor's MM.

Example 5: Optimization of Therapeutic Agent and Drug Delivery Using MEGA-PRESS A patient with Parkinson's disease is treated intranasally with a sol-gel formulation of NAC, NACA, NAC derivative, NAC metabolite, NAC congener, D-NAC, GSH, a GSH derivative, or a pharmaceutically-acceptable salt thereof. MEGA-PRESS is used to quantify the amount of GSH in the substantia nigra and stratum regions of the brain. The therapeutic agent, dose, dosing interval, and dose delivery system are optimized to deliver the greatest amount of GSH to the substantia nigra and stratum regions of the brain to treat Parkinson's disease.

A patient with hemorrhagic stroke is treated intranasally with a sol-gel formulation of NAC, NACA, NAC derivative, NAC metabolite, NAC congener, D-NAC, GSH, a GSH derivative, or a pharmaceutically-acceptable salt thereof. MEGA-PRESS is used to quantify the amount of NAC in regions of the brain. The therapeutic agent, dose, dosing interval, and dose delivery system are optimized to deliver the greatest concentration of NAC at the site of hemorrhage.

EMBODIMENTS

The following non-limiting embodiments provide illustrative examples of the inventions, but do not limit the scope of the invention.

Embodiment 1. A pharmaceutical composition comprising: a) a glutathione precursor; b) a thermoresponsive polymer; and c) a viscosity modifying agent.

Embodiment 2. The pharmaceutical composition of embodiment 1, wherein the glutathione precursor is NAC.

Embodiment 3. The pharmaceutical composition of embodiment 1, wherein the glutathione precursor is NAC amide.

Embodiment 4. The pharmaceutical composition of embodiment 1, wherein the glutathione precursor is a NAC prodrug.

Embodiment 5. The pharmaceutical composition of embodiment 1, wherein the glutathione precursor is a NAC metabolite.

Embodiment 6. The pharmaceutical composition of embodiment 1, wherein the glutathione precursor is a 5-lipoxygenase activating protein (FLAP) inhibitor.

Embodiment 7. The pharmaceutical composition of any one of embodiments 1-6, wherein the glutathione precursor is present the pharmaceutical composition in an amount of from about 5% to about 50% (w/v).

Embodiment 8. The pharmaceutical composition of any one of embodiments 1-7, wherein the glutathione precursor is present the pharmaceutical composition in an amount of about 10% (w/v).

Embodiment 9. The pharmaceutical composition of any one of embodiments 1-7, wherein the glutathione precursor is present the pharmaceutical composition in an amount of about 17% (w/v).

Embodiment 10. The pharmaceutical composition of any one of embodiments 1-7, wherein the glutathione precursor is present the pharmaceutical composition in an amount of about 20% (w/v).

Embodiment 11. The pharmaceutical composition of any one of embodiments 1-7, wherein the glutathione precursor is present the pharmaceutical composition in an amount of about 30% (w/v).

Embodiment 12. The pharmaceutical composition of any one of embodiments 1-11, wherein the thermoresponsive polymer is a poloxamer.

Embodiment 13. The pharmaceutical composition of any one of embodiments 1-12, wherein the thermoresponsive polymer is poloxamer 407.

Embodiment 14. The pharmaceutical composition of any one of embodiments 1-12, wherein the thermoresponsive polymer is poloxamer 338.

Embodiment 15. The pharmaceutical composition of any one of embodiments 1-14, wherein the thermoresponsive polymer is present in the pharmaceutical composition in an amount of from about 5% to about 30% (w/w).

Embodiment 16. The pharmaceutical composition of any one of embodiments 1-15, wherein the thermoresponsive polymer is present in the pharmaceutical composition in an amount of about 10% (w/w).

Embodiment 17. The pharmaceutical composition of any one of embodiments 1-15, wherein the thermoresponsive polymer is present in the pharmaceutical composition in an amount of about 13% (w/w).

Embodiment 18. The pharmaceutical composition of any one of embodiments 1-15, wherein the thermoresponsive polymer is present in the pharmaceutical composition in an amount of about 15% (w/w).

Embodiment 19. The pharmaceutical composition of any one of embodiments 1-18, wherein the viscosity modifying agent is a poloxamer.

Embodiment 20. The pharmaceutical composition of any one of embodiments 1-19, wherein the viscosity modifying agent is poloxamer 188.

Embodiment 21. The pharmaceutical composition of any one of embodiments 1-19, wherein the viscosity modifying agent is poloxamer 237.

Embodiment 22. The pharmaceutical composition of any one of embodiments 1-21, wherein the viscosity modifying agent is present in the pharmaceutical composition in an amount of from about 1.5% to about 10% (w/w).

Embodiment 23. The pharmaceutical composition of any one of embodiments 1-22, wherein the viscosity modifying agent is present in the pharmaceutical composition in an amount of about 2% (w/w).

Embodiment 24. The pharmaceutical composition of any one of embodiments 1-22, wherein the viscosity modifying agent is present in the pharmaceutical composition in an amount of about 2.8% (w/w).

Embodiment 25. The pharmaceutical composition of any one of embodiments 1-22, wherein the viscosity modifying agent is present in the pharmaceutical composition in an amount of about 3.5% (w/w).

Embodiment 26. The pharmaceutical composition of any one of embodiments 1-25, further comprising a mucoadhesive agent.

Embodiment 27. The pharmaceutical composition of embodiment 26, wherein the mucoadhesive agent is a cellulose.

Embodiment 28. The pharmaceutical composition of embodiment 26, wherein the mucoadhesive agent is hydroxypropyl methylcellulose.

Embodiment 29. The pharmaceutical composition of any one of embodiments 26-28, wherein the mucoadhesive agent is present in the pharmaceutical composition in an amount of from about 0.1% to about 0.5% (w/w).

Embodiment 30. The pharmaceutical composition of any one of embodiments 26-29, wherein the mucoadhesive agent is present in the pharmaceutical composition in an amount of about 0.1% (w/w).

Embodiment 31. The pharmaceutical composition of any one of embodiments 1-30, further comprising a preservative.

Embodiment 32. The pharmaceutical composition of embodiment 31, wherein the preservative is methyl paraben.

Embodiment 33. The pharmaceutical composition of embodiment 31, wherein the preservative is propyl paraben.

Embodiment 34. The pharmaceutical composition of any one of embodiments 31-33, wherein the preservative is present in the pharmaceutical composition in an amount of from about 0.1% to about 0.5% (w/w).

Embodiment 35. The pharmaceutical composition of any one of embodiments 31-34, wherein the preservative is present in the pharmaceutical composition in an amount of about 0.1% (w/w).

Embodiment 36. The pharmaceutical composition of any one of embodiments 1-35, wherein the pharmaceutical composition is formulated for intranasal administration.

Embodiment 37. The pharmaceutical composition of any one of embodiments 1-36, wherein the pharmaceutical composition is formulated as a solution.

Embodiment 38. The pharmaceutical composition of any one of embodiments 1-36, wherein the pharmaceutical composition is formulated as a gel.

Embodiment 39. The pharmaceutical composition of any one of embodiments 1-38, wherein the pharmaceutical composition has a gelation temperature of from about 26° C. to about 29° C.

Embodiment 40. The pharmaceutical composition of any one of embodiments 1-39, wherein the pharmaceutical composition has a gelation temperature of about 27.5° C.

Embodiment 41. The pharmaceutical composition of any one of embodiments 1-40, wherein the pharmaceutical has a gel strength at about 34° C. of from about 7335 Pa to about 7465 Pa.

Embodiment 42. The pharmaceutical composition of any one of embodiments 1-41, wherein the pharmaceutical has a gel strength at about 34° C. of about 7400 Pa.

Embodiment 43. The pharmaceutical composition of any one of embodiments 1-42, wherein the pharmaceutical composition has a viscosity at about 34° C. of from about 2 Pa·s to about 2.5 Pa·s.

Embodiment 44. The pharmaceutical composition of any one of embodiments 1-43, wherein the pharmaceutical composition has a viscosity at about 34° C. of about 2.2 Pa·s.

Embodiment 45. A method of treating a condition, the method comprising administering a therapeutically-effective amount of a pharmaceutical composition to a subject in need thereof, the pharmaceutical composition comprising:

a) a glutathione precursor; and b) a thermoresponsive polymer, wherein the administering is intranasal.

Embodiment 46. The method of embodiment 45, wherein the condition is traumatic brain injury.

Embodiment 47. The method of embodiment 45, wherein the condition is post-concussion syndrome.

Embodiment 48. The method of embodiment 45, wherein the condition is a central nervous system disorder.

Embodiment 49. The method of embodiment 45, wherein the condition is a neurodegenerative disease.

Embodiment 50. The method of embodiment 45, wherein the condition is Parkinson's disease.

Embodiment 51. The method of embodiment 45, wherein the condition is Alzheimer's disease.

Embodiment 52. The method of embodiment 45, wherein the condition is brain cancer.

Embodiment 53. The method of embodiment 45, wherein the condition is a mood disorder.

Embodiment 54. The method of embodiment 45, wherein the condition is a psychiatric disorder.

Embodiment 55. The method of embodiment 45, wherein the condition is depression.

Embodiment 56. The method of embodiment 45, wherein the condition is bipolar disorder.

Embodiment 57. The method of embodiment 45, wherein the condition is schizophrenia.

Embodiment 58. The method of any one of embodiments 45-57, wherein the glutathione precursor is NAC.

Embodiment 59. The method of any one of embodiments 45-57, wherein the glutathione precursor is NAC amide.

Embodiment 60. The method of any one of embodiments 45-57, wherein the glutathione precursor is a NAC prodrug.

Embodiment 61. The method of any one of embodiments 45-57, wherein the glutathione precursor is a NAC metabolite.

Embodiment 62. The method of any one of embodiments 45-57, wherein the glutathione precursor is a 5-lipoxygenase activating protein (FLAP) inhibitor.

Embodiment 63. The method of any one of embodiments 45-62, wherein the glutathione precursor is present the pharmaceutical composition in an amount of from about 5% to about 70% (w/v).

Embodiment 64. The method of any one of embodiments 45-63, wherein the glutathione precursor is present the pharmaceutical composition in an amount of about 10% (w/v).

Embodiment 65. The method of any one of embodiments 45-63, wherein the glutathione precursor is present the pharmaceutical composition in an amount of about 17% (w/v).

Embodiment 66. The method of any one of embodiments 45-63, wherein the glutathione precursor is present the pharmaceutical composition in an amount of about 20% (w/v).

Embodiment 67. The method of any one of embodiments 45-63, wherein the glutathione precursor is present the pharmaceutical composition in an amount of about 30% (w/v).

Embodiment 68. The method of any one of embodiments 45-67, wherein the thermoresponsive polymer is a poloxamer.

Embodiment 69. The method of any one of embodiments 45-68, wherein the thermoresponsive polymer is poloxamer 407.

Embodiment 70. The method of any one of embodiments 45-68, wherein the thermoresponsive polymer is poloxamer 338.

Embodiment 71. The method of any one of embodiments 45-70, wherein the thermoresponsive polymer is present in the pharmaceutical composition in an amount of from about 5% to about 30% (w/w).

Embodiment 72. The method of any one of embodiments 45-71, wherein the thermoresponsive polymer is present in the pharmaceutical composition in an amount of about 10% (w/w).

Embodiment 73. The method of any one of embodiments 45-72, wherein the thermoresponsive polymer is present in the pharmaceutical composition in an amount of about 13% (w/w).

Embodiment 74. The method of any one of embodiments 45-72, wherein the thermoresponsive polymer is present in the pharmaceutical composition in an amount of about 15% (w/w).

Embodiment 75. The method of any one of embodiments 45-74, wherein the pharmaceutical composition further comprises a viscosity modifying agent.

Embodiment 76. The method of embodiment 75, wherein the viscosity modifying agent is a poloxamer.

Embodiment 77. The method of embodiment 75 or 76, wherein the viscosity modifying agent is poloxamer 188.

Embodiment 78. The method of embodiment 75 or 76, wherein the viscosity modifying agent is poloxamer 237.

Embodiment 79. The method of any one of embodiments 75-78, wherein the viscosity modifying agent is present in the pharmaceutical composition in an amount of from about 1.5% to about 10% (w/w).

Embodiment 80. The method of any one of embodiments 75-79, wherein the viscosity modifying agent is present in the pharmaceutical composition in an amount of about 2% (w/w).

Embodiment 81. The method of any one of embodiments 75-79, wherein the viscosity modifying agent is present in the pharmaceutical composition in an amount of about 2.8% (w/w).

Embodiment 82. The method of any one of embodiments 75-79, wherein the viscosity modifying agent is present in the pharmaceutical composition in an amount of about 3.5% (w/w).

Embodiment 83. The method of any one of embodiments 45-82, wherein the pharmaceutical composition further comprises a mucoadhesive agent.

Embodiment 84. The method of embodiment 83, wherein the mucoadhesive agent is a cellulose.

Embodiment 85. The method of embodiment 83, wherein the mucoadhesive agent is hydroxypropyl methylcellulose.

Embodiment 86. The method of any one of embodiments 83-85, wherein the mucoadhesive agent is present in the pharmaceutical composition in an amount of from about 0.1% to about 0.5% (w/w).

Embodiment 87. The method of any one of embodiments 83-86, wherein the mucoadhesive agent is present in the pharmaceutical composition in an amount of about 0.1% (w/w).

Embodiment 88. The method of any one of embodiments 45-87, wherein the pharmaceutical composition further comprises a preservative.

Embodiment 89. The method of embodiment 88, wherein the preservative is methyl paraben.

Embodiment 90. The method of embodiment 88, wherein the preservative is propyl paraben.

Embodiment 91. The method of any one of embodiments 88-90, wherein the preservative is present in the pharmaceutical composition in an amount of from about 0.1% to about 0.5% (w/w).

Embodiment 92. The method of any one of embodiments 88-91, wherein the preservative is present in the pharmaceutical composition in an amount of about 0.1% (w/w).

Embodiment 93. The method of any one of embodiments 45-92, wherein the pharmaceutical composition is formulated as a solution.

Embodiment 94. The method of any one of embodiments 45-92, wherein the pharmaceutical composition is formulated as a gel.

Embodiment 95. The method of any one of embodiments 45-94, wherein the therapeutically-effective amount comprises from about 50 mg to about 500 mg of the glutathione precursor.

Embodiment 96. The method of any one of embodiments 45-95, wherein the therapeutically-effective amount comprises about 100 mg of the glutathione precursor.

Embodiment 97. The method of any one of embodiments 45-95, wherein the therapeutically-effective amount comprises about 400 mg of the glutathione precursor.

Embodiment 98. The method of any one of embodiments 45-97, wherein the administering is by an atomizer.

Embodiment 99. The method of any one of embodiments 45-97, wherein the administering is by a nebulizer.

Embodiment 100. The method of any one of embodiments 45-97, wherein the administering is by a nasal pump.

Embodiment 101. The method of any one of embodiments 45-100, wherein the administering increases a concentration of GSH in a brain region by at least about 5%.

Embodiment 102. The method of any one of embodiments 45-100, wherein the administering increases a concentration of GSH in a brain region by at least about 10%.

Embodiment 103. The method of any one of embodiments 45-100, wherein the administering increases a concentration of GSH in a brain region by at least about 15%.

Embodiment 104. The method of any one of embodiments 45-103, wherein the administering the pharmaceutical composition is to an upper region of a nasal cavity of the subject.

Embodiment 105. The method of any one of embodiments 45-104, wherein the administering delivers the pharmaceutical composition from a nose of the subject to a brain region of the subject.

Embodiment 106. The method of embodiment 105, wherein the brain region is a cerebrum.

Embodiment 107. The method of embodiment 105, wherein the brain region is a cerebellum.

Embodiment 108. A method of treating a condition, the method comprising administering a therapeutically-effective amount of a pharmaceutical composition to a subject in need thereof, the pharmaceutical composition comprising:

a) a glutathione precursor;

b) a thermoresponsive polymer; and c) a viscosity modifying agent.

Embodiment 109. The method of embodiment 108, the condition is traumatic brain injury.

Embodiment 110. The method of embodiment 108, wherein the condition is post-concussion syndrome.

Embodiment 111. The method of embodiment 108, wherein the condition is a central nervous system disorder.

Embodiment 112. The method of embodiment 108, wherein the condition is a neurodegenerative disease.

Embodiment 113. The method of embodiment 108, wherein the condition is Parkinson's disease.

Embodiment 114. The method of embodiment 108, wherein the condition is Alzheimer's disease.

Embodiment 115. The method of embodiment 108, wherein the condition is brain cancer.

Embodiment 116. The method of embodiment 108, wherein the condition is a mood disorder.

Embodiment 117. The method of embodiment 108, wherein the condition is a psychiatric disorder.

Embodiment 118. The method of embodiment 108, wherein the condition is depression.

Embodiment 119. The method of embodiment 108, wherein the condition is bipolar disorder.

Embodiment 120. The method of embodiment 108, wherein the condition is schizophrenia.

Embodiment 121. The method of any one of embodiments 108-120, wherein the administering is intranasal.

Embodiment 122. The method of any one of embodiments 108-121, wherein the subject is human.

Embodiment 123. The method of any one of embodiments 108-122, wherein the glutathione precursor is NAC.

Embodiment 124. The method of any one of embodiments 108-122, wherein the glutathione precursor is NAC amide.

Embodiment 125. The method of any one of embodiments 108-122, wherein the glutathione precursor is a NAC prodrug.

Embodiment 126. The method of any one of embodiments 108-122, wherein the glutathione precursor is a NAC metabolite.

Embodiment 127. The method of any one of embodiments 108-122, wherein the glutathione precursor is a 5-lipoxygenase activating protein (FLAP) inhibitor.

Embodiment 128. The method of any one of embodiments 108-127, wherein the glutathione precursor is present the pharmaceutical composition in an amount of from about 5% to about 50% (w/v).

Embodiment 129. The method of any one of embodiments 108-128, wherein the glutathione precursor is present the pharmaceutical composition in an amount of about 10% (w/v).

Embodiment 130. The method of any one of embodiments 108-128, wherein the glutathione precursor is present the pharmaceutical composition in an amount of about 17% (w/v).

Embodiment 131. The method of any one of embodiments 108-128, wherein the glutathione precursor is present the pharmaceutical composition in an amount of about 20% (w/v).

Embodiment 132. The method of any one of embodiments 108-128, wherein the glutathione precursor is present the pharmaceutical composition in an amount of about 30% (w/v).

Embodiment 133. The method of any one of embodiments 108-132, wherein the thermoresponsive polymer is a poloxamer.

Embodiment 134. The method of any one of embodiments 108-133, wherein the thermoresponsive polymer is poloxamer 407.

Embodiment 135. The method of any one of embodiments 108-133, wherein the thermoresponsive polymer is poloxamer 338.

Embodiment 136. The method of any one of embodiments 108-135, wherein the thermoresponsive polymer is present in the pharmaceutical composition in an amount of from about 5% to about 30% (w/w).

Embodiment 137. The method of any one of embodiments 108-136, wherein the thermoresponsive polymer is present in the pharmaceutical composition in an amount of about 10% (w/w).

Embodiment 138. The method of any one of embodiments 108-136, wherein the thermoresponsive polymer is present in the pharmaceutical composition in an amount of about 13% (w/w).

Embodiment 139. The method of any one of embodiments 108-136, wherein the thermoresponsive polymer is present in the pharmaceutical composition in an amount of about 15% (w/w).

Embodiment 140. The method of any one of embodiments 108-139, wherein the viscosity modifying agent is a poloxamer.

Embodiment 141. The method of any one of embodiments 108-140, wherein the viscosity modifying agent is poloxamer 188.

Embodiment 142. The method of any one of embodiments 108-140, wherein the viscosity modifying agent is poloxamer 237.

Embodiment 143. The method of any one of embodiments 108-142, wherein the viscosity modifying agent is present in the pharmaceutical composition in an amount of from about 1.5% to about 10% (w/w).

Embodiment 144. The method of any one of embodiments 108-143, wherein the viscosity modifying agent is present in the pharmaceutical composition in an amount of about 2% (w/w).

Embodiment 145. The method of any one of embodiments 108-143, wherein the viscosity modifying agent is present in the pharmaceutical composition in an amount of about 2.8% (w/w).

Embodiment 146. The method of any one of embodiments 108-143, wherein the viscosity modifying agent is present in the pharmaceutical composition in an amount of about 3.5% (w/w).

Embodiment 147. The method of any one of embodiments 108-146, further comprising a mucoadhesive agent.

Embodiment 148. The method of embodiment 147, wherein the mucoadhesive agent is a cellulose.

Embodiment 149. The method of embodiment 147, wherein the mucoadhesive agent is hydroxypropyl methylcellulose.

Embodiment 150. The method of any one of embodiments 147-149, wherein the mucoadhesive agent is present in the pharmaceutical composition in an amount of from about 0.1% to about 0.5% (w/w).

Embodiment 151. The method of any one of embodiments 147-150, wherein the mucoadhesive agent is present in the pharmaceutical composition in an amount of about 0.1% (w/w).

Embodiment 152. The method of any one of embodiments 108-151, further comprising a preservative.

Embodiment 153. The method of embodiment 152, wherein the preservative is methyl paraben.

Embodiment 154. The method of embodiment 152, wherein the preservative is propyl paraben.

Embodiment 155. The method of any one of embodiments 152-154, wherein the preservative is present in the pharmaceutical composition in an amount of from about 0.1% to about 0.5% (w/w).

Embodiment 156. The method of any one of embodiments 152-155, wherein the preservative is present in the pharmaceutical composition in an amount of about 0.1% (w/w).

Embodiment 157. The method of any one of embodiments 108-156, wherein the pharmaceutical composition is formulated as a solution.

Embodiment 158. The method of any one of embodiments 108-156, wherein the pharmaceutical composition is formulated as a gel.

Embodiment 159. The method of any one of embodiments 108-158, wherein the therapeutically-effective amount comprises from about 50 mg to about 500 mg of the glutathione precursor.

Embodiment 160. The method of any one of embodiments 108-159, wherein the therapeutically-effective amount comprises about 100 mg of the glutathione precursor.

Embodiment 161. The method of any one of embodiments 108-159, wherein the therapeutically-effective amount comprises about 400 mg of the glutathione precursor.

Embodiment 162. The method of any one of embodiments 108-161, wherein the administering is by an atomizer.

Embodiment 163. The method of any one of embodiments 108-161, wherein the administering is by a nebulizer.

Embodiment 164. The method of any one of embodiments 108-161, wherein the administering is by a nasal pump.

Embodiment 165. The method of any one of embodiments 108-164, wherein the administering increases a concentration of GSH in a brain region by at least about 5%.

Embodiment 166. The method of any one of embodiments 108-164, wherein the administering increases a concentration of GSH in a brain region by at least about 10%.

Embodiment 167. The method of any one of embodiments 108-164, wherein the administering increases a concentration of GSH in a brain region by at least about 15%.

Embodiment 168. The method of any one of embodiments 108-167, wherein the administering the pharmaceutical composition is to an upper region of a nasal cavity of the subject.

Embodiment 169. The method of any one of embodiments 108-168, wherein the administering delivers the pharmaceutical composition from a nose of the subject to a brain region of the subject.

Embodiment 170. The method of embodiment 169, wherein the brain region is a cerebrum.

Embodiment 171. The method of embodiment 169, wherein the brain region is a cerebellum.

Embodiment 172. A method of treating a condition, the method comprising administering a therapeutically-effective amount of a pharmaceutical composition to a subject in need thereof, the pharmaceutical composition comprising: a) a glutathione precursor; and b) a thermoresponsive polymer, wherein the condition is a central nervous system condition.

Embodiment 173. The method of embodiment 172, wherein the central nervous system condition is traumatic brain injury.

Embodiment 174. The method of embodiment 172, wherein the central nervous system condition is post-concussion syndrome.

Embodiment 175. The method of embodiment 172, wherein the central nervous system condition is epilepsy.

Embodiment 176. The method of embodiment 172, wherein the central nervous system condition is Alzheimer's disease.

Embodiment 177. The method of embodiment 172, wherein the central nervous system condition is Parkinson's disease.

Embodiment 178. The method of embodiment 172, wherein the central nervous system condition is brain cancer.

Embodiment 179. The method of any one of embodiments 172-178, wherein the glutathione precursor is NAC.

Embodiment 180. The method of any one of embodiments 172-178, wherein the glutathione precursor is NAC amide.

Embodiment 181. The method of any one of embodiments 172-178, wherein the glutathione precursor is a NAC prodrug.

Embodiment 182. The method of any one of embodiments 172-178, wherein the glutathione precursor is a NAC metabolite.

Embodiment 183. The method of any one of embodiments 172-178, wherein the glutathione precursor is a 5-lipoxygenase activating protein (FLAP) inhibitor.

Embodiment 184. The method of any one of embodiments 172-183, wherein the glutathione precursor is present the pharmaceutical composition in an amount of from about 5% to about 70% (w/v).

Embodiment 185. The method of any one of embodiments 172-184, wherein the glutathione precursor is present the pharmaceutical composition in an amount of about 10% (w/v).

Embodiment 186. The method of any one of embodiments 172-184, wherein the glutathione precursor is present the pharmaceutical composition in an amount of about 17% (w/v).

Embodiment 187. The method of any one of embodiments 172-184, wherein the glutathione precursor is present the pharmaceutical composition in an amount of about 20% (w/v).

Embodiment 188. The method of any one of embodiments 172-184, wherein the glutathione precursor is present the pharmaceutical composition in an amount of about 30% (w/v).

Embodiment 189. The method of any one of embodiments 172-188, wherein the thermoresponsive polymer is a poloxamer.

Embodiment 190. The method of any one of embodiments 172-189, wherein the thermoresponsive polymer is poloxamer 407.

Embodiment 191. The method of any one of embodiments 172-189, wherein the thermoresponsive polymer is poloxamer 338.

Embodiment 192. The method of any one of embodiments 172-191, wherein the thermoresponsive polymer is present in the pharmaceutical composition in an amount of from about 5% to about 30% (w/w).

Embodiment 193. The method of any one of embodiments 172-192, wherein the thermoresponsive polymer is present in the pharmaceutical composition in an amount of about 10% (w/w).

Embodiment 194. The method of any one of embodiments 172-193, wherein the thermoresponsive polymer is present in the pharmaceutical composition in an amount of about 13% (w/w).

Embodiment 195. The method of any one of embodiments 172-193, wherein the thermoresponsive polymer is present in the pharmaceutical composition in an amount of about 15% (w/w).

Embodiment 196. The method of any one of embodiments 172-195, wherein the pharmaceutical composition further comprises a viscosity modifying agent.

Embodiment 197. The method of embodiment 196, wherein the viscosity modifying agent is a poloxamer.

Embodiment 198. The method of embodiment 196 or 197, wherein the viscosity modifying agent is poloxamer 188.

Embodiment 199. The method of embodiment 196 or 197, wherein the viscosity modifying agent is poloxamer 237.

Embodiment 200. The method of any one of embodiments 196-199, wherein the viscosity modifying agent is present in the pharmaceutical composition in an amount of from about 1.5% to about 10% (w/w).

Embodiment 201. The method of any one of embodiments 196-200, wherein the viscosity modifying agent is present in the pharmaceutical composition in an amount of about 2% (w/w).

Embodiment 202. The method of any one of embodiments 196-200, wherein the viscosity modifying agent is present in the pharmaceutical composition in an amount of about 2.8% (w/w).

Embodiment 203. The method of any one of embodiments 196-200, wherein the viscosity modifying agent is present in the pharmaceutical composition in an amount of about 3.5% (w/w).

Embodiment 204. The method of any one of embodiments 172-203, wherein the pharmaceutical composition further comprises a mucoadhesive agent.

Embodiment 205. The method of embodiment 204, wherein the mucoadhesive agent is a cellulose.

Embodiment 206. The method of embodiment 204, wherein the mucoadhesive agent is hydroxypropyl methylcellulose.

Embodiment 207. The method of any one of embodiments 204-206, wherein the mucoadhesive agent is present in the pharmaceutical composition in an amount of from about 0.1% to about 0.5% (w/w).

Embodiment 208. The method of any one of embodiments 204-207, wherein the mucoadhesive agent is present in the pharmaceutical composition in an amount of about 0.1% (w/w).

Embodiment 209. The method of any one of embodiments 172-208, wherein the pharmaceutical composition further comprises a preservative.

Embodiment 210. The method of embodiment 209, wherein the preservative is methyl paraben.

Embodiment 211. The method of embodiment 209, wherein the preservative is propyl paraben.

Embodiment 212. The method of any one of embodiments 209-211, wherein the preservative is present in the pharmaceutical composition in an amount of from about 0.1% to about 0.5% (w/w).

Embodiment 213. The method of any one of embodiments 209-212, wherein the preservative is present in the pharmaceutical composition in an amount of about 0.1% (w/w).

Embodiment 214. The method of any one of embodiments 172-213, wherein the pharmaceutical composition is formulated as a solution.

Embodiment 215. The method of any one of embodiments 172-213, wherein the pharmaceutical composition is formulated as a gel.

Embodiment 216. The method of any one of embodiments 172-215, wherein the therapeutically-effective amount comprises from about 50 mg to about 500 mg of the glutathione precursor.

Embodiment 217. The method of any one of embodiments 172-216, wherein the therapeutically-effective amount comprises about 100 mg of the glutathione precursor.

Embodiment 218. The method of any one of embodiments 172-216, wherein the therapeutically-effective amount comprises about 400 mg of the glutathione precursor.

Embodiment 219. The method of any one of embodiments 172-218, wherein the administering is by an atomizer.

Embodiment 220. The method of any one of embodiments 172-218, wherein the administering is by a nebulizer.

Embodiment 221. The method of any one of embodiments 172-218, wherein the administering is by a nasal pump.

Embodiment 222. The method of any one of embodiments 172-221, wherein the administering increases a concentration of GSH in a brain region by at least about 5%.

Embodiment 223. The method of any one of embodiments 172-221, wherein the administering increases a concentration of GSH in a brain region by at least about 10%.

Embodiment 224. The method of any one of embodiments 172-221, wherein the administering increases a concentration of GSH in a brain region by at least about 15%.

Embodiment 225. The method of any one of embodiments 172-224, wherein the administering the pharmaceutical composition is to an upper region of a nasal cavity of the subject.

Embodiment 226. The method of any one of embodiments 172-225, wherein the administering delivers the pharmaceutical composition from a nose of the subject to a brain region of the subject.

Embodiment 227. The method of embodiment 226, wherein the brain region is a cerebrum.

Embodiment 228. The method of embodiment 226, wherein the brain region is a cerebellum.

Embodiment 229. A method of treating a condition, the method comprising administering a therapeutically-effective amount of a pharmaceutical composition to a subject in need thereof, the pharmaceutical composition comprising:

a) a glutathione precursor; and b) a thermoresponsive polymer, wherein the condition is a head condition.

Embodiment 230. The method of embodiment 229, wherein the head condition is traumatic brain injury.

Embodiment 231. The method of embodiment 229, wherein the head condition is post-concussion syndrome.

Embodiment 232. The method of embodiment 229, wherein the head condition is a central nervous system disorder.

Embodiment 233. The method of embodiment 229, wherein the head condition is a neurodegenerative disorder.

Embodiment 234. The method of embodiment 229, wherein the head condition is Parkinson's disease.

Embodiment 235. The method of embodiment 229, wherein the head condition is Alzheimer's disease.

Embodiment 236. The method of embodiment 229, wherein the head condition is brain cancer.

Embodiment 237. The method of embodiment 229, wherein the head condition is a mood disorder.

Embodiment 238. The method of embodiment 229, wherein the head condition is a psychiatric disorder.

Embodiment 239. The method of embodiment 229, wherein the head condition is depression.

Embodiment 240. The method of embodiment 229, wherein the head condition is bipolar disorder.

Embodiment 241. The method of embodiment 229, wherein the head condition is schizophrenia.

Embodiment 242. The method of any one of embodiments 229-241, wherein the glutathione precursor is NAC.

Embodiment 243. The method of any one of embodiments 229-241, wherein the glutathione precursor is NAC amide.

Embodiment 244. The method of any one of embodiments 229-241, wherein the glutathione precursor is a NAC prodrug.

Embodiment 245. The method of any one of embodiments 229-241, wherein the glutathione precursor is a NAC metabolite.

Embodiment 246. The method of any one of embodiments 229-241, wherein the glutathione precursor is a 5-lipoxygenase activating protein (FLAP) inhibitor.

Embodiment 247. The method of any one of embodiments 229-246, wherein the glutathione precursor is present the pharmaceutical composition in an amount of from about 5% to about 50% (w/v).

Embodiment 248. The method of any one of embodiments 229-247, wherein the glutathione precursor is present the pharmaceutical composition in an amount of about 10% (w/v).

Embodiment 249. The method of any one of embodiments 229-247, wherein the glutathione precursor is present the pharmaceutical composition in an amount of about 17% (w/v).

Embodiment 250. The method of any one of embodiments 229-247, wherein the glutathione precursor is present the pharmaceutical composition in an amount of about 20% (w/v).

Embodiment 251. The method of any one of embodiments 229-247, wherein the glutathione precursor is present the pharmaceutical composition in an amount of about 30% (w/v).

Embodiment 252. The method of any one of embodiments 229-251, wherein the thermoresponsive polymer is a poloxamer.

Embodiment 253. The method of any one of embodiments 229-252, wherein the thermoresponsive polymer is poloxamer 407.

Embodiment 254. The method of any one of embodiments 229-252, wherein the thermoresponsive polymer is poloxamer 338.

Embodiment 255. The method of any one of embodiments 229-254, wherein the thermoresponsive polymer is present in the pharmaceutical composition in an amount of from about 5% to about 30% (w/w).

Embodiment 256. The method of any one of embodiments 229-255, wherein the thermoresponsive polymer is present in the pharmaceutical composition in an amount of about 10% (w/w).

Embodiment 257. The method of any one of embodiments 229-255, wherein the thermoresponsive polymer is present in the pharmaceutical composition in an amount of about 13% (w/w).

Embodiment 258. The method of any one of embodiments 229-255, wherein the thermoresponsive polymer is present in the pharmaceutical composition in an amount of about 15% (w/w).

Embodiment 259. The method of any one of embodiments 229-258, wherein the pharmaceutical composition further comprises a viscosity modifying agent.

Embodiment 260. The method of embodiment 259, wherein the viscosity modifying agent is a poloxamer.

Embodiment 261. The method of embodiment 259 or 260, wherein the viscosity modifying agent is poloxamer 188.

Embodiment 262. The method of embodiment 259 or 260, wherein the viscosity modifying agent is poloxamer 237.

Embodiment 263. The method of any one of embodiments 259-262, wherein the viscosity modifying agent is present in the pharmaceutical composition in an amount of from about 1.5% to about 10% (w/w).

Embodiment 264. The method of any one of embodiments 259-263, wherein the viscosity modifying agent is present in the pharmaceutical composition in an amount of about 2% (w/w).

Embodiment 265. The method of any one of embodiments 259-263, wherein the viscosity modifying agent is present in the pharmaceutical composition in an amount of about 2.8% (w/w).

Embodiment 266. The method of any one of embodiments 259-263, wherein the viscosity modifying agent is present in the pharmaceutical composition in an amount of about 3.5% (w/w).

Embodiment 267. The method of any one of embodiments 229-266, wherein the pharmaceutical composition further comprises a mucoadhesive agent.

Embodiment 268. The method of embodiment 267, wherein the mucoadhesive agent is a cellulose.

Embodiment 269. The method of embodiment 267, wherein the mucoadhesive agent is hydroxypropyl methylcellulose.

Embodiment 270. The method of any one of embodiments 267-269, wherein the mucoadhesive agent is present in the pharmaceutical composition in an amount of from about 0.1% to about 0.5% (w/w).

Embodiment 271. The method of any one of embodiments 267-270, wherein the mucoadhesive agent is present in the pharmaceutical composition in an amount of about 0.1% (w/w).

Embodiment 272. The method of any one of embodiments 229-271, wherein the pharmaceutical composition further comprises a preservative.

Embodiment 273. The method of embodiment 272, wherein the preservative is methyl paraben.

Embodiment 274. The method of embodiment 272, wherein the preservative is propyl paraben.

Embodiment 275. The method of any one of embodiments 272-274, wherein the preservative is present in the pharmaceutical composition in an amount of from about 0.1% to about 0.5% (w/w).

Embodiment 276. The method of any one of embodiments 272-275, wherein the preservative is present in the pharmaceutical composition in an amount of about 0.1% (w/w).

Embodiment 277. The method of any one of embodiments 229-276, wherein the pharmaceutical composition is formulated as a solution.

Embodiment 278. The method of any one of embodiments 229-276, wherein the pharmaceutical composition is formulated as a gel.

Embodiment 279. The method of any one of embodiments 229-278, wherein the therapeutically-effective amount comprises from about 50 mg to about 500 mg of the glutathione precursor.

Embodiment 280. The method of any one of embodiments 229-279, wherein the therapeutically-effective amount comprises about 100 mg of the glutathione precursor.

Embodiment 281. The method of any one of embodiments 229-279, wherein the therapeutically-effective amount comprises about 400 mg of the glutathione precursor.

Embodiment 282. The method of any one of embodiments 229-281, wherein the administering is intranasal.

Embodiment 283. The method of any one of embodiments 229-282, wherein the administering is by an atomizer.

Embodiment 284. The method of any one of embodiments 229-282, wherein the administering is by a nebulizer.

Embodiment 285. The method of any one of embodiments 229-282, wherein the administering is by a nasal pump.

Embodiment 286. The method of any one of embodiments 229-285, wherein the administering increases a concentration of GSH in a brain region by at least about 5%.

Embodiment 287. The method of any one of embodiments 229-285, wherein the administering increases a concentration of GSH in a brain region by at least about 10%.

Embodiment 288. The method of any one of embodiments 229-285, wherein the administering increases a concentration of GSH in a brain region by at least about 15%.

Embodiment 289. The method of any one of embodiments 229-288, wherein the administering the pharmaceutical composition is to an upper region of a nasal cavity of the subject.

Embodiment 290. The method of any one of embodiments 229-289, wherein the administering delivers the pharmaceutical composition from a nose of the subject to a brain region of the subject.

Embodiment 291. The method of embodiment 290, wherein the brain region is a cerebrum.

Embodiment 292. The method of embodiment 290, wherein the brain region is a cerebellum.

Embodiment 293. The method of embodiment 229, wherein the subject is human.

Embodiment 294. A method of treating a condition, the method comprising administering a therapeutically-effective amount of a pharmaceutical composition to a human subject in need thereof, the pharmaceutical composition comprising: a) a glutathione precursor; and b) a thermoresponsive polymer.

Embodiment 295. The method of embodiment 294, wherein the condition is traumatic brain injury.

Embodiment 296. The method of embodiment 294, wherein the condition is post-concussion syndrome.

Embodiment 297. The method of embodiment 294, wherein the condition is a central nervous system disorder.

Embodiment 298. The method of embodiment 294, wherein the condition is a neurodegenerative disorder.

Embodiment 299. The method of embodiment 294, wherein the condition is Parkinson's disease.

Embodiment 300. The method of embodiment 294, wherein the condition is Alzheimer's disease.

Embodiment 301. The method of embodiment 294, wherein the condition is brain cancer.

Embodiment 302. The method of embodiment 294, wherein the condition is a mood disorder.

Embodiment 303. The method of embodiment 294, wherein the condition is a psychiatric disorder.

Embodiment 304. The method of embodiment 294, wherein the condition is depression.

Embodiment 305. The method of embodiment 294, wherein the condition is bipolar disorder.

Embodiment 306. The method of embodiment 294, wherein the condition is schizophrenia.

Embodiment 307. The method of any one of embodiments 294-306, wherein the glutathione precursor is NAC.

Embodiment 308. The method of any one of embodiments 294-306, wherein the glutathione precursor is NAC amide.

Embodiment 309. The method of any one of embodiments 294-306, wherein the glutathione precursor is a NAC prodrug.

Embodiment 310. The method of any one of embodiments 294-306, wherein the glutathione precursor is a NAC metabolite.

Embodiment 311. The pharmaceutical composition of any one of embodiments 294-306, wherein the glutathione precursor is a 5-lipoxygenase activating protein (FLAP) inhibitor.

Embodiment 312. The method of any one of embodiments 294-311, wherein the glutathione precursor is present the pharmaceutical composition in an amount of from about 5% to about 50% (w/v).

Embodiment 313. The method of any one of embodiments 294-312, wherein the glutathione precursor is present the pharmaceutical composition in an amount of about 10% (w/v).

Embodiment 314. The method of any one of embodiments 294-312, wherein the glutathione precursor is present the pharmaceutical composition in an amount of about 17% (w/v).

Embodiment 315. The method of any one of embodiments 294-312, wherein the glutathione precursor is present the pharmaceutical composition in an amount of about 20% (w/v).

Embodiment 316. The method of any one of embodiments 294-312, wherein the glutathione precursor is present the pharmaceutical composition in an amount of about 30% (w/v).

Embodiment 317. The method of any one of embodiments 294-316, wherein the thermoresponsive polymer is a poloxamer.

Embodiment 318. The method of embodiment 294, wherein the thermoresponsive polymer is poloxamer 407.

Embodiment 319. The method of embodiment 294, wherein the thermoresponsive polymer is poloxamer 338.

Embodiment 320. The method of any one of embodiments 294-319, wherein the thermoresponsive polymer is present in the pharmaceutical composition in an amount of from about 5% to about 30% (w/w).

Embodiment 321. The method of any one of embodiments 294-320, wherein the thermoresponsive polymer is present in the pharmaceutical composition in an amount of about 10% (w/w).

Embodiment 322. The method of any one of embodiments 294-320, wherein the thermoresponsive polymer is present in the pharmaceutical composition in an amount of about 13% (w/w).

Embodiment 323. The method of any one of embodiments 294-320, wherein the thermoresponsive polymer is present in the pharmaceutical composition in an amount of about 15% (w/w).

Embodiment 324. The method of any one of embodiments 294-323, wherein the pharmaceutical composition further comprises a viscosity modifying agent.

Embodiment 325. The method of embodiment 324, wherein the viscosity modifying agent is a poloxamer.

Embodiment 326. The method of embodiment 324 or 325, wherein the viscosity modifying agent is poloxamer 188.

Embodiment 327. The method of embodiment 324 or 325, wherein the viscosity modifying agent is poloxamer 237.

Embodiment 328. The method of any one of embodiments 324-327, wherein the viscosity modifying agent is present in the pharmaceutical composition in an amount of from about 1.5% to about 10% (w/w).

Embodiment 329. The method of any one of embodiments 324-328, wherein the viscosity modifying agent is present in the pharmaceutical composition in an amount of about 2% (w/w).

Embodiment 330. The method of any one of embodiments 324-329, wherein the viscosity modifying agent is present in the pharmaceutical composition in an amount of about 2.8% (w/w).

Embodiment 331. The method of any one of embodiments 324-329, wherein the viscosity modifying agent is present in the pharmaceutical composition in an amount of about 3.5% (w/w).

Embodiment 332. The method of any one of embodiments 294-331, wherein the pharmaceutical composition further comprises a mucoadhesive agent.

Embodiment 333. The method of embodiment 332, wherein the mucoadhesive agent is a cellulose.

Embodiment 334. The method of embodiment 332, wherein the mucoadhesive agent is hydroxypropyl methylcellulose.

Embodiment 335. The method of any one of embodiments 332-334, wherein the mucoadhesive agent is present in the pharmaceutical composition in an amount of from about 0.1% to about 0.5% (w/w).

Embodiment 336. The method of any one of embodiments 332-335, wherein the mucoadhesive agent is present in the pharmaceutical composition in an amount of about 0.1% (w/w).

Embodiment 337. The method of any one of embodiments 294-336, wherein the pharmaceutical composition further comprises a preservative.

Embodiment 338. The method of embodiment 333, wherein the preservative is methyl paraben.

Embodiment 339. The method of embodiment 333, wherein the preservative is propyl paraben.

Embodiment 340. The method of any one of embodiments 333-339, wherein the preservative is present in the pharmaceutical composition in an amount of from about 0.1% to about 0.5% (w/w).

Embodiment 341. The method of any one of embodiments 333-340, wherein the preservative is present in the pharmaceutical composition in an amount of about 0.1% (w/w).

Embodiment 342. The method of any one of embodiments 294-241, wherein the pharmaceutical composition is formulated as a solution.

Embodiment 343. The method of any one of embodiments 294-241, wherein the pharmaceutical composition is formulated as a gel.

Embodiment 344. The method of any one of embodiments 294-343, wherein the therapeutically-effective amount comprises from about 50 mg to about 500 mg of the glutathione precursor.

Embodiment 345. The method of any one of embodiments 294-344, wherein the therapeutically-effective amount comprises about 100 mg of the glutathione precursor.

Embodiment 346. The method of any one of embodiments 294-344, wherein the therapeutically-effective amount comprises about 400 mg of the glutathione precursor.

Embodiment 347. The method of any one of embodiments 294-346, wherein the administering is intranasal.

Embodiment 348. The method of any one of embodiments 294-347, wherein the administering is by an atomizer.

Embodiment 349. The method of any one of embodiments 294-347, wherein the administering is by a nebulizer.

Embodiment 350. The method of any one of embodiments 294-347, wherein the administering is by a nasal pump.

Embodiment 351. The method of any one of embodiments 294-350, wherein the administering increases a concentration of GSH in a brain region by at least about 5%.

Embodiment 352. The method of any one of embodiments 294-350, wherein the administering increases a concentration of GSH in a brain region by at least about 10%.

Embodiment 353. The method of any one of embodiments 294-350, wherein the administering increases a concentration of GSH in a brain region by at least about 15%.

Embodiment 354. The method of any one of embodiments 294-353, wherein the administering the pharmaceutical composition is to an upper region of a nasal cavity of the subject.

Embodiment 355. The method of any one of embodiments 294-354, wherein the administering delivers the pharmaceutical composition from a nose of the subject to a brain region of the subject.

Embodiment 356. The method of embodiment 355, wherein the brain region is a cerebrum.

Embodiment 357. The method of embodiment 355, wherein the brain region is a cerebellum.

Embodiment 358. A pharmaceutical composition comprising: (a) a glutathione precursor; (b) a mucoadhesive agent; and (c) a preservative.

Embodiment 359. The pharmaceutical composition of embodiment 358, wherein the glutathione precursor is NAC.

Embodiment 360. The pharmaceutical composition of embodiment 358, wherein the glutathione precursor is NAC amide.

Embodiment 361. The pharmaceutical composition of embodiment 358, wherein the glutathione precursor is a 5-lipoxygenase activating protein (FLAP) inhibitor.

Embodiment 362. The pharmaceutical composition of any one of embodiments 358-361, wherein the glutathione precursor is present in the pharmaceutical composition in an amount of from about 5% to about 70% (w/v).

Embodiment 363. The pharmaceutical composition of any one of embodiments 358-362, wherein the glutathione precursor is present in the pharmaceutical composition in an amount of about 40% (w/v).

Embodiment 364. The pharmaceutical composition of any one of embodiments 358-363, wherein the mucoadhesive agent is a cellulose.

Embodiment 365. The pharmaceutical composition any one of embodiments 358-363, wherein the mucoadhesive agent is hydroxypropyl methylcellulose.

Embodiment 366. The pharmaceutical composition of any one of embodiments 358-365, wherein the mucoadhesive agent is present in the pharmaceutical composition in an amount of from about 0.1% to about 0.5% (w/w).

Embodiment 367. The pharmaceutical composition of any one of embodiments 358-366, wherein the preservative is present in the pharmaceutical composition in an amount of from about 0.1% to about 0.5% (w/w).

Embodiment 368. The pharmaceutical composition of any one of embodiments 358-367, wherein the preservative is a paraben.

Embodiment 369. The pharmaceutical composition of any one of embodiments 358-368, wherein the preservative is methyl paraben.

Embodiment 370. The pharmaceutical composition of any one of embodiments 358-368, wherein the preservative is propyl paraben.

Embodiment 371. The pharmaceutical composition of any one of embodiments 358-370, wherein the preservative is a combination of two parabens.

Embodiment 372. The pharmaceutical composition of any one of embodiments 358-371, wherein the combination of two parabens comprises two different parabens.

Embodiment 373. The pharmaceutical composition of any one of embodiments 358-372, wherein the preservative is a combination of three parabens.

Embodiment 374. The pharmaceutical composition of any one of embodiments 358-373, wherein the combination of three parabens comprises three different parabens.

Embodiment 375. The pharmaceutical composition of any one of embodiments 358-374, wherein the composition further comprises an additional preservative.

Embodiment 376. The pharmaceutical composition of any one of embodiments 358-375, wherein the composition further comprises a thermoresponsive polymer.

Embodiment 377. The pharmaceutical composition of any one of embodiments 358-376, wherein the composition further comprises a viscosity modifying agent.

Embodiment 378. The pharmaceutical composition of any one of embodiments 358-377, wherein the pharmaceutical composition is formulated for intranasal administration.

Embodiment 379. The pharmaceutical composition of any one of embodiments 358-378, wherein the pharmaceutical composition is formulated as a solution.

Embodiment 380. The pharmaceutical composition of any one of embodiments 358-379, wherein the pharmaceutical composition has a gelation temperature of from about 26° C. to about 29° C.

Embodiment 381. The pharmaceutical composition of any one of embodiments 358-380, wherein the pharmaceutical has a gel strength at about 34° C. of from about 7335 Pa to about 7465 Pa.

Embodiment 382. The pharmaceutical composition of any one of embodiments 358-381, wherein the pharmaceutical composition has a viscosity at about 34° C. of from about 2 Pa·s to about 2.5 Pa·s.

What is claimed is:

1. A pharmaceutical composition formulated for intranasal administration, the composition comprising:

a) from about 10% to about 20% (w/w) N-acetylcysteine;

b) from about 10% to about 15% (w/w) of poloxamer 407;

c) from about 2% to about 4% (w/w) of poloxamer 188; and d) from about 0.1% to about 0.5% (w/w) of a mucoadhesive agent;

wherein the composition exists as a liquid at room temperature and forms a gel upon administration having a gelation temperature of from about 26° C. to about 29° C., a gel strength at 34° C. of from 7335 Pa to 7465 Pa, and a viscosity at 34° C. of from 2.0 Pa·s to 2.5 Pa·s.

2. The pharmaceutical composition of claim 1, wherein the N-acetylcysteine is present in the pharmaceutical composition in an amount of about 10% (w/v).

3. The pharmaceutical composition of claim 1, wherein the N-acetylcysteine is present in the pharmaceutical composition in an amount of about 17% (w/v).

4. The pharmaceutical composition of claim 1, further comprising a preservative.

5. The pharmaceutical composition of claim 4, wherein the preservative is present in the pharmaceutical composition in an amount of from about 0.1% to about 0.5% (w/w).

6. The pharmaceutical composition of claim 1, wherein the mucoadhesive agent is hydroxypropyl methylcellulose.

7. The pharmaceutical composition of claim 6, wherein the N-acetylcysteine is present in an amount of 16.6% (w/w), the poloxamer 407 is present in an amount of 13.0% (w/w), the poloxamer 188 is present in an amount of 2.8% (w/w), and the mucoadhesive agent is hydroxypropyl methylcellulose and is present in an amount of 0.1% (w/w).

* * * * *